United States Patent
Voegele et al.

(10) Patent No.: US 8,812,100 B2
(45) Date of Patent: Aug. 19, 2014

(54) DEVICE AND METHOD FOR SELF-POSITIONING OF A STIMULATION DEVICE TO ACTIVATE BROWN ADIPOSE TISSUE DEPOT IN A SUPRACLAVICULAR FOSSA REGION

(75) Inventors: James W. Voegele, Cincinnati, OH (US); Thomas E. Albrecht, Campbell, CA (US); Tamara C. Baynham, Liberty Township, OH (US); David Cagle, East Hampton, CT (US); Anthony R. DiUbaldi, Jackson, NJ (US); Jason L. Harris, Mason, OH (US); Michael A. Murray, Bellevue, KY (US); Mark S. Zeiner, Mason, OH (US); Jacob Crabtree, Hixson, TN (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 0 days.

(21) Appl. No.: 13/468,858

(22) Filed: May 10, 2012

(65) Prior Publication Data
US 2013/0304175 A1    Nov. 14, 2013

(51) Int. Cl.
*A61N 1/00*    (2006.01)
(52) U.S. Cl.
USPC ............................................. 607/2; 607/152
(58) Field of Classification Search
USPC ............................ 607/115, 142, 148–156, 2; 600/382–393
See application file for complete search history.

(56) References Cited

U.S. PATENT DOCUMENTS

| | | | |
|---|---|---|---|
| 6,445,955 B1* | 9/2002 | Michelson et al. | ............. 607/46 |
| 6,645,229 B2 | 11/2003 | Matsumura | |
| 7,599,743 B2 | 10/2009 | Hassler, Jr. et al. | |
| 7,647,112 B2 | 1/2010 | Tracey et al. | |
| 7,979,137 B2 | 7/2011 | Tracey et al. | |
| 2005/0177067 A1 | 8/2005 | Tracey et al. | |
| 2006/0195153 A1 | 8/2006 | DiUbaldi et al. | |
| 2007/0185541 A1 | 8/2007 | DiUbaldi et al. | |
| 2008/0132962 A1 | 6/2008 | DiUbaldi et al. | |
| 2008/0147146 A1 | 6/2008 | Wahlgren et al. | |
| 2009/0093858 A1 | 4/2009 | DiUbaldi | |

(Continued)

FOREIGN PATENT DOCUMENTS

JP    2001259047    9/2001

OTHER PUBLICATIONS

Co-pending, co-owned U.S. Appl. No. 12/980,695, filed Dec. 29, 2010.

(Continued)

*Primary Examiner* — Scott Getzow
(74) *Attorney, Agent, or Firm* — Cohen & Hilderbrand, PLLC

(57) ABSTRACT

Self-positioning of at least a portion of a transdermal electrical stimulation patch within a target area (e.g., supraclavicular fossa region) of a human body to activate a depot of brown adipose tissue therein. An electric field is generated using the electrical stimulation patch to activate the brown adipose tissue within the supraclavicular fossa region of the body. The patch is self-positioned using one or more anatomical points (e.g., anatomical landmarks and/or anatomical features) or markings on the body. Brown adipose tissue may also be activated by applying an electrical signal to a body piercing partially implanted proximate a target area in which the tissue is disposed.

10 Claims, 21 Drawing Sheets

(56) References Cited

U.S. PATENT DOCUMENTS

| | | | |
|---|---|---|---|
| 2009/0132018 A1 | 5/2009 | DiUbaldi et al. | |
| 2009/0149918 A1 | 6/2009 | Krulevitch et al. | |
| 2009/0157149 A1 | 6/2009 | Wahlgren et al. | |
| 2010/0056433 A1 | 3/2010 | Sensfuss | |
| 2010/0161001 A1 | 6/2010 | DiUbaldi et al. | |
| 2010/0161005 A1 | 6/2010 | Wahlgren et al. | |
| 2010/0222734 A1* | 9/2010 | Jayes et al. | 604/20 |
| 2010/0239648 A1 | 9/2010 | Smith et al. | |
| 2010/0249677 A1 | 9/2010 | DiUbaldi et al. | |
| 2010/0312295 A1 | 12/2010 | Vase et al. | |
| 2011/0094773 A1 | 4/2011 | Bare et al. | |
| 2011/0152987 A1* | 6/2011 | Wahlgren et al. | 607/115 |
| 2011/0237922 A1* | 9/2011 | Parker et al. | 600/382 |
| 2011/0263490 A1 | 10/2011 | Kaplan et al. | |
| 2011/0270360 A1* | 11/2011 | Harris et al. | 607/62 |
| 2013/0110220 A1* | 5/2013 | Brown | 607/149 |

OTHER PUBLICATIONS

Co-pending, co-owned U.S. Appl. No. 12/980,710, filed Dec. 29, 2010.

Copending, co-owned U.S. Appl. No. 61/427,968, filed Dec. 29, 2010.

Co-pending, co-owned U.S. Appl. No. 13/977,543, filed Jun. 28, 2013.

Copending, co-owned U.S. Appl. No. 61/428,013, filed Dec. 29, 2010.

Copending, co-owned U.S. Appl. No. 61/428,008, filed Dec. 29, 2010.

Copending, co-owned U.S. Appl. No. 61/427,991, filed Dec. 29, 2010.

Copending, co-owned U.S. Appl. No. 13/977,501, filed Oct. 2, 2013.

M. Toii et al. "Fall in Skin Temperature of Exercising Man," Br. J. Sp. Med. (1992); 26(1), pp. 29-32.

Fruhbeck et al., BAT: a new target for human obesity?, Trends in Pharmacological Sciences, vol. 30, No. 8, pp. 387-396 (2009).

Enerback, Sven, "The Origins of Brown Adipose Tissue," The New England Journal of Medicine, vol. 360 (19), May 7, 2009, pp. 2021-2023.

Cannon et al., "Nonshivering Thermogenesis and its Adequate Measurement in Metabolic Studies," The Journal of Experimental Biology, 214 (2011) pp. 242-253.

Cannon et al., "Brown Adipose Tissue Function and Physiological Significance," Physiol. Rev., 84 (2004) pp. 277-359.

* cited by examiner

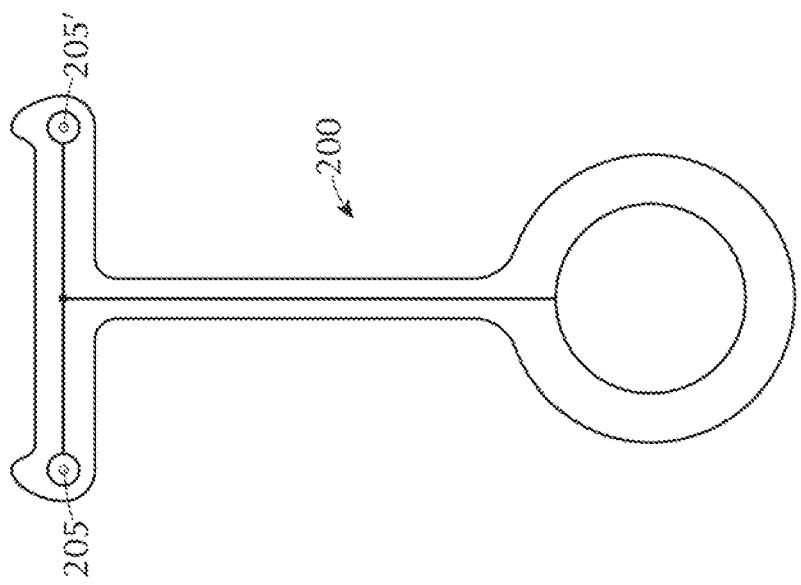
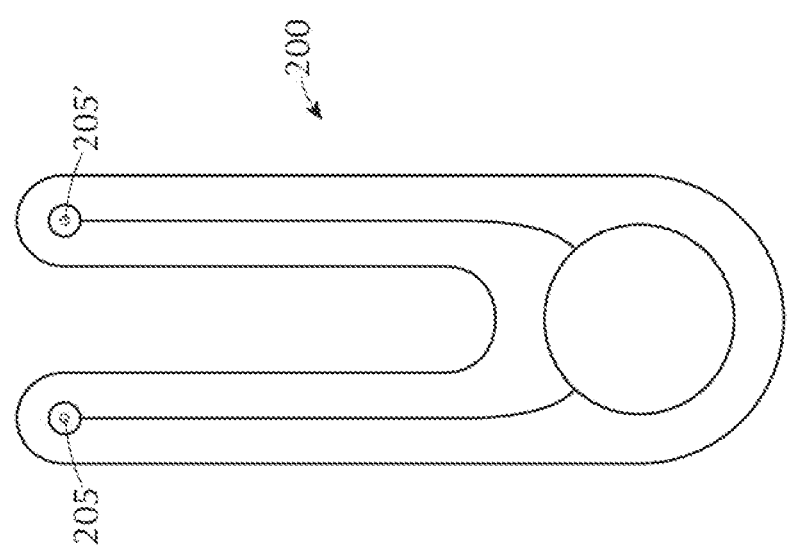

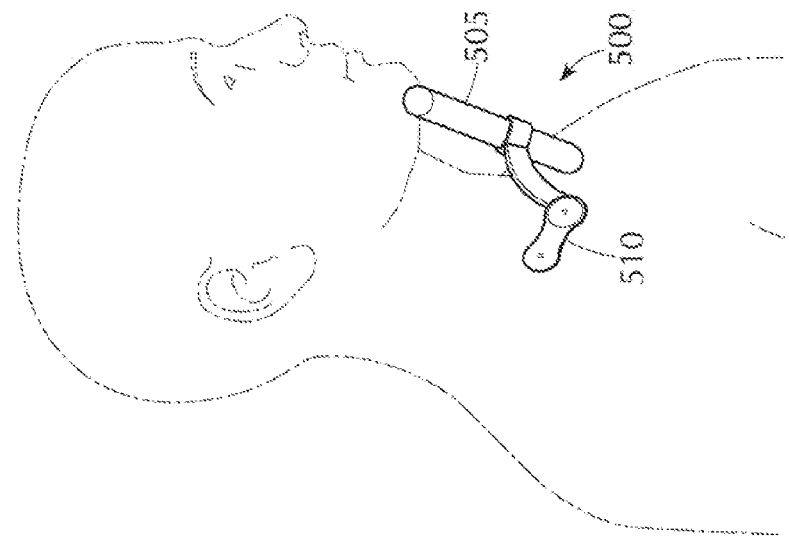
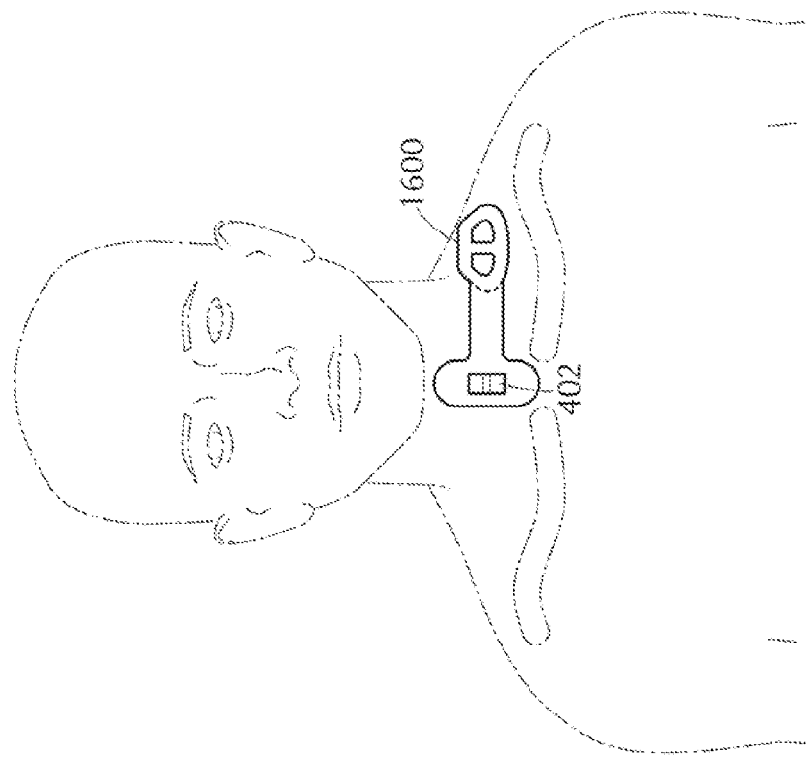

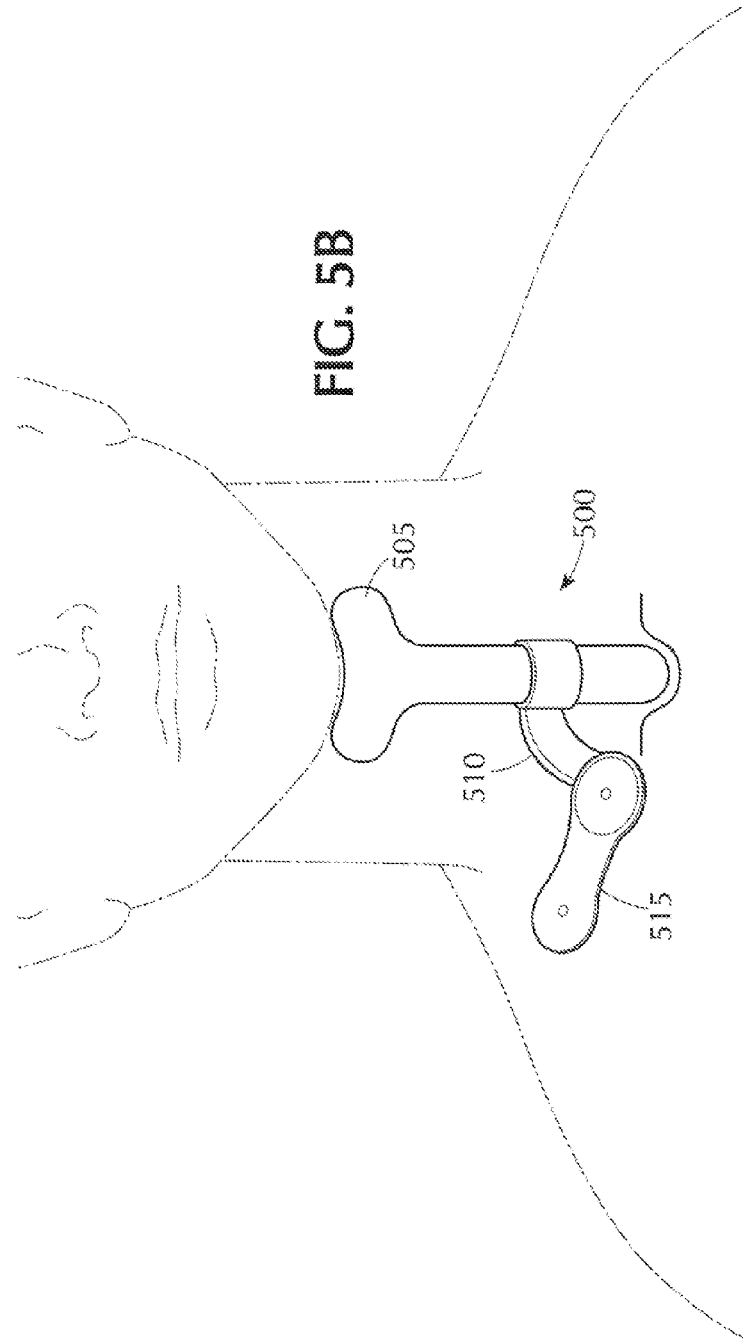

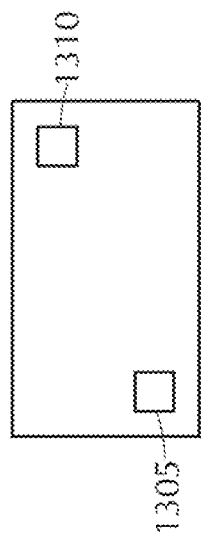
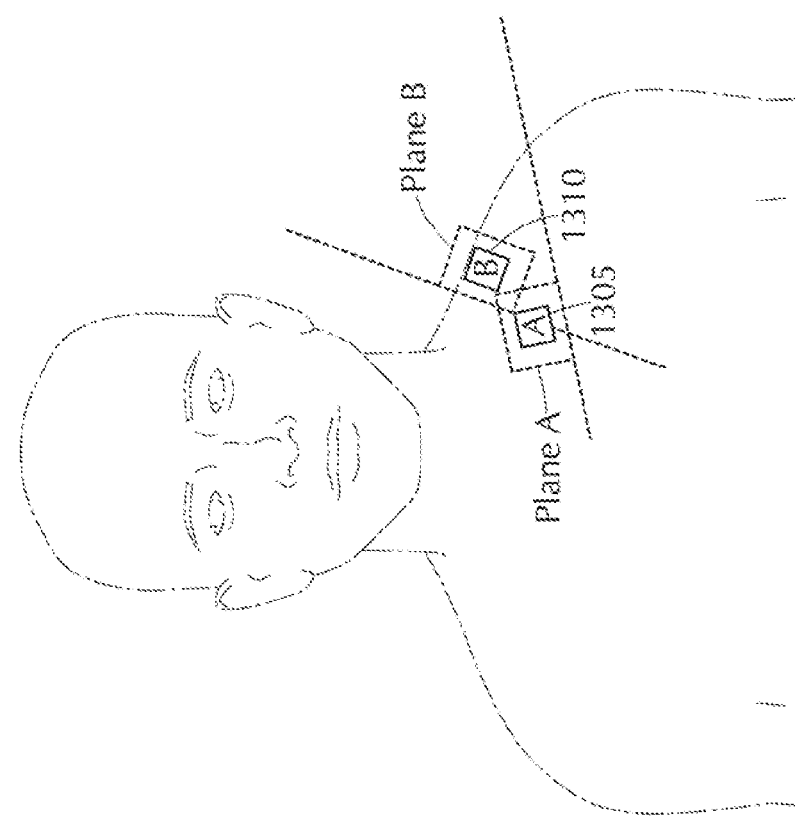
FIG. 13B
FIG. 13A

DEVICE AND METHOD FOR SELF-POSITIONING OF A STIMULATION DEVICE TO ACTIVATE BROWN ADIPOSE TISSUE DEPOT IN A SUPRACLAVICULAR FOSSA REGION

BACKGROUND OF THE INVENTION

1. Field of the Invention

The present invention is directed to a non-invasive stimulation device for activation of Brown Adipose Tissue (BAT) in a supraclavicular fossa region (as defined below) of the human body. Furthermore, the present invention also relates to a methodology for proper positioning of at least a portion of the patch within the supraclavicular fossa region to stimulate the sympathetic nerves and thereby activate a BAT deposit therein.

2. Description of Related Art

Obesity is becoming a growing concern, particularly in the United States, as the number of people with obesity continues to increase and more is learned about the negative health effects of obesity. Severe obesity, in which a person is 100 pounds or more over ideal body weight, in particular poses significant risks for severe health problems. Accordingly, a great deal of attention is being focused on treating obese patients.

Surgical procedures to treat severe obesity have included various forms of gastric and intestinal bypasses (stomach stapling), biliopancreatic diversion, adjustable gastric banding, vertical banded gastroplasty, gastric plications, and sleeve gastrectomies (removal of all or a portion of the stomach). Such surgical procedures have increasingly been performed laparoscopically. Reduced postoperative recovery time, markedly decreased post-operative pain and wound infection, and improved cosmetic outcome are well established benefits of laparoscopic surgery, derived mainly from the ability of laparoscopic surgeons to perform an operation utilizing smaller incisions in the body cavity wall. However, such surgical procedures risk a variety of complications during surgery, pose undesirable post-operative consequences such as pain and cosmetic scarring, and often require lengthy periods of patient recovery. Patients with obesity thus rarely seek or accept surgical intervention, with only about 1% of patients with obesity being surgically treated for this disorder. Furthermore, even if successfully performed and initial weight loss occurs, surgical intervention to treat obesity may not result in lasting weight loss, thereby requiring additional different obesity treatment.

Nonsurgical procedures for treating obesity have also been developed. However, effective therapies for increasing energy expenditure leading to improvements in metabolic outcomes, e.g., weight loss, have focused on pharmaceutical approaches, which have various technical and physiological limitations.

It has been recognized in, for example, U.S. Pat. No. 6,645,229, filed Dec. 20, 2000, entitled "Slimming Device", which is herein incorporated by reference, that brown adipose tissue (BAT) plays a role in the regulation of energy expenditure and that stimulating BAT can result in patient slimming. BAT activation is regulated by the sympathetic nervous system and other physiological, e.g., hormonal and metabolic, influences. When activated, BAT removes free fatty acids (FFA) and oxygen from the blood supply for the generation of heat. The oxidative phosphorylation cycle that occurs in the mitochondria of activated BAT is shown and described in U.S. Pat. No. 6,645,229.

Accordingly, there is a need for improved methods and devices for treating obesity and in particular for activating BAT. The present invention focuses on activation of BAT via external electrical stimulation of sympathetic nerves innervating BAT and/or the brown adipocytes directly. It is desirable to develop a system and method for proper self-positioning of a transdermal electrical stimulation patch for activation of a target BAT depot within the human body. Furthermore, it is also desirable for the transdermal electrical stimulation patch to be relatively inexpensive, require minimal instruction, able to be self-administered without requiring assistance from a third person and be consistently accurate in its proper placement on the human body.

SUMMARY OF THE INVENTION

The present invention is directed to a system and method for self-positioning at least a portion of a transdermal electrical stimulation patch within a target area of a human body to activate a depot of BAT therein. Specifically, the invention relates to self-positioning of a transdermal electrical stimulation patch within the supraclavicular fossa region of a human body to activate a depot of BAT therein.

In particular, the present invention is directed to a method for self-positioning of at least a portion of a transdermal electrical stimulation patch within a supraclavicular fossa region of a human body to activate a depot of brown adipose tissue therein. An electric field is generated using the electrical stimulation patch to activate the brown adipose tissue within the supraclavicular fossa region of the body. The patch is self-positioned using one or more anatomical points (e.g., anatomical landmarks and/or anatomical features) or markings on the body. Brown adipose tissue may also be activated by applying an electrical signal to a body piercing object partially implanted proximate a target area in which the tissue is disposed.

Yet another aspect of the present invention relates to a method for properly self-positioning a transdermal electrical stimulation patch to activate brown adipose tissue depot in a supraclavicular fossa region of a human body. Initially, at least a portion of the transdermal electrical stimulation patch is self-positioned within the supraclavicular fossa region of the body. An electric field is then generated using the electrical stimulation patch to activate the brown adipose tissue within the supraclavicular fossa region of the body.

In one particular aspect of the invention, the transdermal electrical stimulation patch is self-positioned by referencing one or more anatomical points on the body, wherein each anatomical point on the body represents an anatomical landmark or an anatomical feature.

In another aspect of the invention, the transdermal electrical stimulation patch is self-positioned using a separate mechanical locating tool that references the one or more anatomical points on the body to properly position the electrical stimulation patch to activate the BAT depot in the supraclavicular fossa region.

Still in yet another aspect of the invention, the transdermal electrical stimulation patch is self-positioned by aligning at least one window or opening defined in the patch with the one or more anatomical points on the body.

One other aspect of the present invention is directed to a transdermal electrical stimulation patch for activation of the brown adipose tissue depot in the supraclavicular fossa region of the body in accordance with the method discussed in the preceding paragraphs, wherein the patch includes an electrical signal waveform generator; and at least one electrode for producing the electric field for transcutaneously activating the brown adipose tissue depot in the supraclavicular fossa region.

A particular aspect of the invention relates to the transdermal electrical stimulation patch for activation of the brown adipose tissue depot in the supraclavicular fossa region of the body, wherein the patch includes more than one electrode. The patch may be properly positioned on the body such that: (i) all of the electrodes lay within the supraclavicular fossa region; (ii) all of the electrodes, electronics and power source lay within the supraclavicular fossa region; (iii) at least one electrode lay within the supraclavicular fossa region, while some combination of one or more electrodes, electronics and a power source lay outside the supraclavicular fossa region; or (iv) all of the electrodes, electronics and a power source lay outside the supraclavicular fossa region.

While still another aspect of the present invention is related to a transdermal electrical stimulation patch for activation of the brown adipose tissue depot in the supraclavicular fossa region of the body, wherein the patch includes more than one electrode; and when the patch is properly positioned on the body the electrodes are disposed in more than one plane.

Another aspect of the present invention relates to a method for activation of brown adipose tissue depot in a human body by partially implanting a body piercing object proximate a target area of the body in which the brown adipose tissue depot is located. An electrical stimulation signal is applied to the body piercing object to generate an electric field to activate the brown adipose tissue depot.

BRIEF DESCRIPTION OF THE DRAWING

The foregoing and other features of the present invention will be more readily apparent from the following detailed description and drawings of illustrative embodiments of the invention wherein like reference numbers refer to similar elements throughout the several views and in which:

FIG. 2G is yet another exemplary ti-shaped configuration of the BAT activation transdermal electrical stimulating patch in accordance with the present invention wherein independent electrical paths are connected to each of the two respective electrodes;

FIG. 2H is one other exemplary configuration of the BAT activation transdermal electrical stimulating patch in accordance with the present invention wherein a single electrical path is connected to the two electrodes;

FIG. 4B is the patch illustrates the patch in FIG. 4A adhered to and properly positioned on the body with the keyhole substantially aligned with a placement sticker adhered to the body at an anatomical recess defined at the junction of the right and left clavicles to insure proper positioning of at least a part of the second portion of the patch within the BAT supraclavicular fossa region;

FIG. 5A is a side view of a mechanical device for proper placement of at least a portion of a BAT activation transdermal electrical stimulating patch in the supraclavicular fossa region of the body utilizing the chin and sternum as anatomical features;

FIG. 5B is a front view of the mechanical tool in FIG. 5A;

FIG. 13A represents a front view of an exemplary BAT transdermal electrical stimulating patch in accordance with the present invention worn on the left hand side of the body wherein the two electrodes are located in different planes;

FIG. 13B represents the BAT transdermal electrical stimulating patch in FIG. 13A;

DETAILED DESCRIPTION OF THE INVENTION

Figure 14:
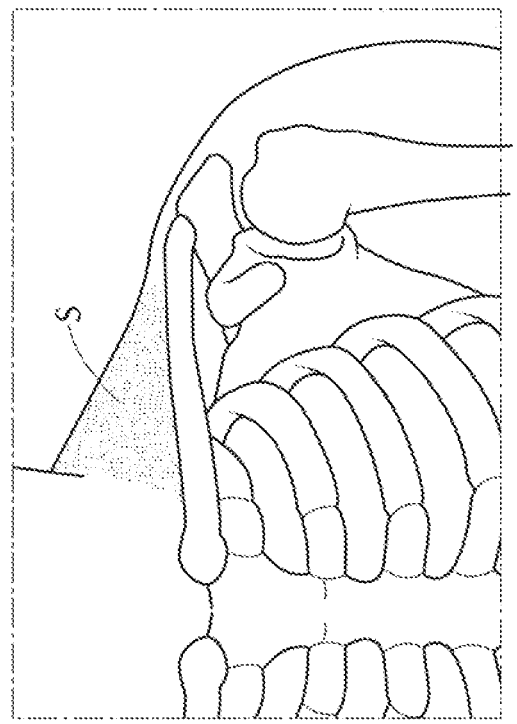
FIG. 14 illustrates an anatomical supraclavicular fossa target area or region of the human body.

Brown Adipose Tissue (BAT) is found in depots throughout the human body. The greatest BAT volume is usually located in an area of the human body referred to as a "supraclavicular fossa" defined herein as a 3-sided area or region bounded by the neck, the clavicle and the trapezius (as illustrated by reference element "S" in FIG. 14). Such definition may be expanded to also include the region extending posteriorly over the trapezius and anteriorly over the clavicle. Aside from having the greatest BAT volume, another consideration in targeting the supraclavicular fossa area of the body is the minimal presence of nerves compared to other BAT depots that may unintentionally be stimulated with undesirable consequences when attempting to activate the BAT therein. The invention has been described and illustrated with respect to stimulation of BAT depot in the supraclavicular fossa region of the human body; however, the devices, systems, processes and methods described herein may be applied to stimulate BAT depot anywhere in the human body.

The present inventive system and method for electrically stimulating a target BAT depot in the body is designed to be relatively inexpensive to manufacture, require minimal instruction, able to be self-administered without requiring assistance from a third person and be consistently accurate when self-positioned on the body.

The invention relates to the stimulation of nerves using techniques such as that disclosed in the following commonly assigned issued U.S. Patents and U.S. Patent Application Publications: U.S. patent application Ser. No. 12/980,695, filed Dec. 29, 2010, entitled "Obesity Therapy and Heart Rate Variability"; U.S. patent application Ser. No. 12/980,710, filed Dec. 29, 2010, entitled "Obesity Therapy and Heart Rate Variability"; U.S. Provisional Patent Application No. 61/427,968, filed Dec. 29, 2010, entitled "Brown Adipocyte Modification"; U.S. Provisional Patent Application No. 61/428,013, filed Dec. 29, 2010, entitled "Methods and Devices for Activating Brown Adipose Tissue"; U.S. Provisional Patent Application Ser. No. 61/428,008, filed Dec. 29, 2010, entitled "Methods and Devices for Activating Brown Adipose Tissue With Light"; U.S. Provisional Patent Application Ser. No. 61/427,991, filed Dec. 29, 2010, entitled "Methods and Devices for Activating Brown Adipose Tissue With Targeted Substance Delivery"; U.S. Pat. No. 7,599,743, issued on Oct. 6, 2009, entitled "Low Frequency Transcutaneous Telemetry to Implanted Medical Device"; U.S. Pat. No. 7,647,112, issued on Jan. 12, 2010, entitled "System and Method of Stimulating a Pudendal or Sacral Nerve Using Conductive Gel Pathway"; U.S. Pat. No. 7,979,137, issued on Jul. 12, 2011, entitled "System and Method for Nerve Stimulation"; U.S. Patent Application Publication No. 2005/01770006667, published on Aug. 11, 2005, entitled "System and Method for Urodynamic Evaluation Utilizing Micro-Electronic Mechanical System"; U.S. Patent Application Publication No. 2006/0195153, published on Aug. 31, 2006, entitled "System and Method for Selectively Stimulating Different Body Parts"; U.S. Patent Application Publication No. 2007/018551, published on Aug. 9, 2007, entitled "Conductive Mesh for Neurostimulation"; U.S. Patent Application Publication No. 2008/0132962, published on Jun. 8, 2008, entitled "System and Method for Affecting Gastric Functions"; U.S. Patent Application Publication No. 2008/0147146, published on Jun. 19, 2008, entitled "Electrode Patch and Method for Neurostimulation"; U.S. Patent Application Publication No. 2009/0093858, published on Apr. 9, 2009, entitled "Implantable Pulse Generator and Methods for Selective Nerve Stimulation"; U.S. Patent Application Publication No. 2009/0132018, published on May 21, 2009, entitled "Nerve Stimulation Patches and Methods for Stimulating Selected Nerves"; U.S. Patent Application Publication No. 2009/0149918, published on Jun. 11, 2009, entitled "Implantable Antenna"; U.S. Patent Application Publication No. 2009/0157149, published on Jun. 18, 2009, entitled "Dermatome Stimulation Devices and Methods"; U.S. Patent Application Publication No. 2010/0056433, published on Mar. 4, 2010, entitled "Novel Peptides for Use in the Treatment of Obesity"; U.S. Patent Application Publication No. 2010/0161001, published on Jun. 24, 2010, entitled "Optimizing Stimulus Current in a Surface Based Stimulation Device"; U.S. Patent Application Publication. No. 2010/0161005, published on Jun. 24, 2010, entitled "Optimizing Stimulation Therapy of an External Stimulating Device Based on Firing of an Action Potential in Target Nerve"; U.S. Patent Application Publication No. 2010/0239648, published on Sep. 23, 2010, entitled "Self Locating, Multiple Application and Multiple Location Medical Patch System and Methods Therefore"; U.S. Patent Application Publication No. 2010/0249677, published on Sep. 30, 2010, entitled "Piezoelectric Stimulation Device"; U.S. Patent Application Publication No. 2011/0094773, published on Apr. 28, 2011, entitled "Offset Electrode"; U.S. Patent Application Publication No. 2011/0152987, published on Jun. 23, 2011, entitled "Placement Devices That Enable Patients to Accurately Position Medical Patches at Target Location and Methods Therefor"; U.S. Patent Application Publication No. 2011/0263490, published on Oct. 27, 2011, entitled "Diagnostic Methods and Combination Therapies Involving MC4R"; U.S. Patent Application Publication No. 2011/0270360, published on Nov. 3, 2011, entitled "Methods and Devices for Activating Brown Adipose Tissue Using Electrical Energy", the disclosures of which are each hereby incorporated by reference in their entirety.

One aspect of the present invention is directed to a neurostimulation device for transcutaneously activating BAT using a non-invasive surface based transdermal electrical stimulating device having one or more electrodes disposed within an area referred to as a stimulating area. Activation of targeted BAT depot may be enhanced or supplemented with non-electrical stimulation such as a pharmacological/chemical substance, magnetic, light or any combination thereof. Preferably at least a portion, most preferably all, of the stimulating area is positioned within the targeted BAT area, (e.g., the supraclavicular fossa area) of the body. The patch may alternatively be positioned on the body such that the stimulating area is positioned entirely outside, but proximate to, the targeted BAT area; however, such placement of the patch would require greater power to activate the target BAT volume possibly resulting in the unintentional stimulation of other nerves. In a preferred embodiment, the external transdermal electrical stimulation device is configured as a patch having one side at least partially coated with a relatively weak adhesive, such as the Adhesive Laminate (Arcare 92587) supplied by Adhesives Research, Inc; Glen Rock, Pa., for releasably adhering to the skin at a desired location for a predetermined period of time. In addition to its securing properties, the adhesive also serves as a barrier for the hydrogel. The adhesive does not have the same constraints or boundaries regarding its placement as that of the electrodes, accordingly, the adhesive may be applied, as desired, keeping in mind such factors as the ability to maintain the patch in place once properly positioned on the body and preventing the hydrogel from washing out. The efficacy of the therapy provided by the BAT electrical stimulation patch is at least in part dependent on positioning of the electrical stimulation area of the patch (including one or more electrodes) over at least a portion of the supraclavicular fossa region of the body. Consistent placement of the BAT stimulating patch with each use is desirable to standardize treatment or therapy.

Figure 1:
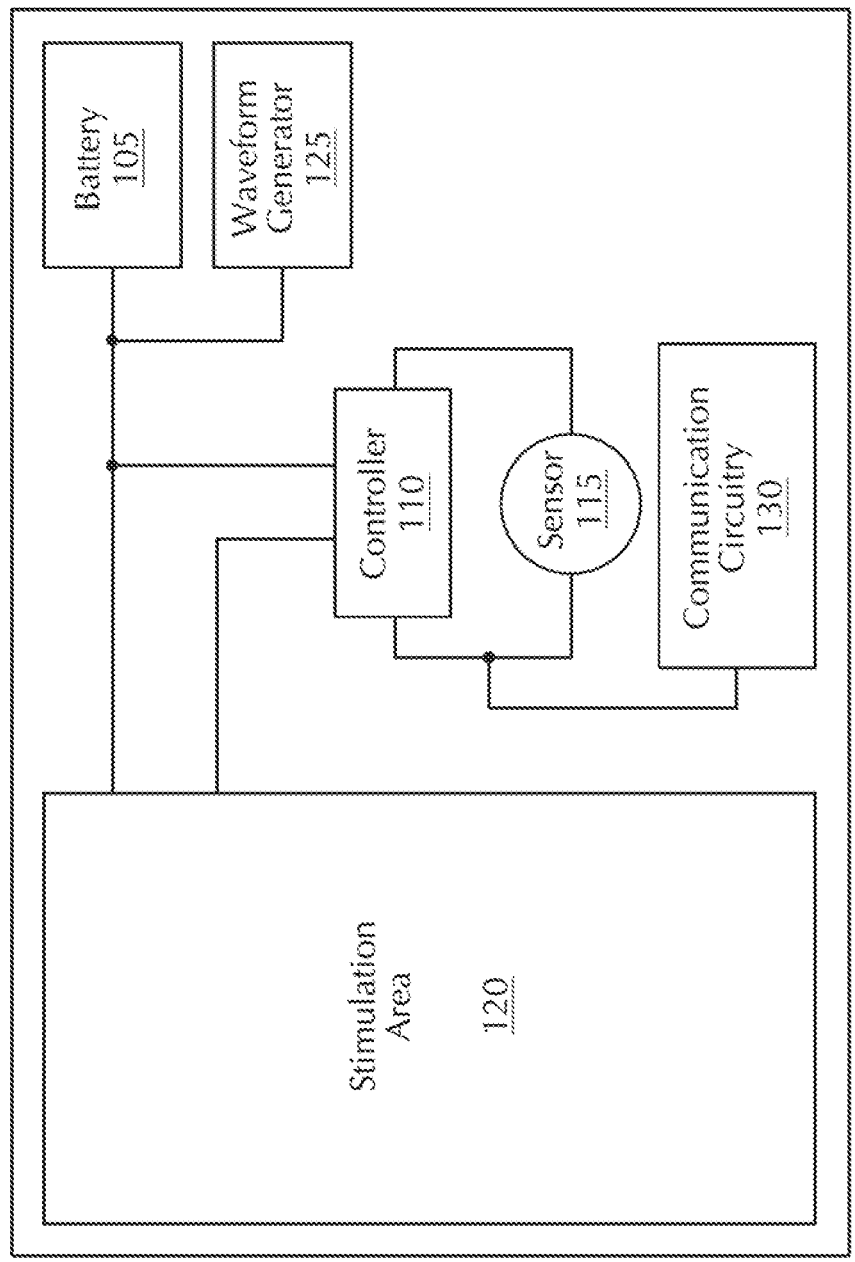
FIG. 1 is an exemplary schematic diagram of the BAT activation transdermal electrical stimulating patch in accordance with the present invention.

FIG. 1 is an exemplary schematic diagram of the transdermal BAT activation electrical simulator patch 100 that includes electronic circuitry powered by a power source (e.g., battery) 105. Despite the fact that the power source 105 forms part of the patch in FIG. 1, this need not always be the case, in that the power source may be separate from the patch itself. The electronic circuitry includes a controller (e.g., processor, microprocessor, microcontroller, CPU, etc.) 110 and one or more waveform generators 125 for producing an electrical stimulation waveform signal. A sensor 115 may also be employed for detecting one or more physical parameters, for example, voltage, current, impedance, temperature, time, salinity, pH, concentration of hormones/chemicals or surface moisture. Data detected by the patch may be transmitted via a closed-loop feedback signal to controller 110 to adjust one or more characteristics (e.g., toggle electric field ON/OFF, intensity, duration or frequency of the electric field) associated with the electrical stimulation waveform signal being generated. Stimulation area 120 includes one or more electrodes in a predetermined pattern or configuration to generate an electric field and activate the targeted BAT volume in the supraclavicular fossa region of the body. The number and arrangement of the electrodes may vary, as desired. It may be desirable for the patch 100 to transmit and/or receive information to/from another electronic device such as, but not limited to, a central server, processor or hand-held controller. In such case, patch 100 may also include communication circuitry 130 such as a transmitter and/or receiver for communicating with that other electronic device. Communication may be over a tethered wire-line connection or wireless interface. Stored or real-time data may be communicated from the patch to the other electronic device. For instance, data transmitted from the patch generally includes one or more physical parameters detected by a sensor; while data received by the stimulation device typically represent control signals for adjusting a parameter associated with the electric field generated or updated software.

Figure 15A:
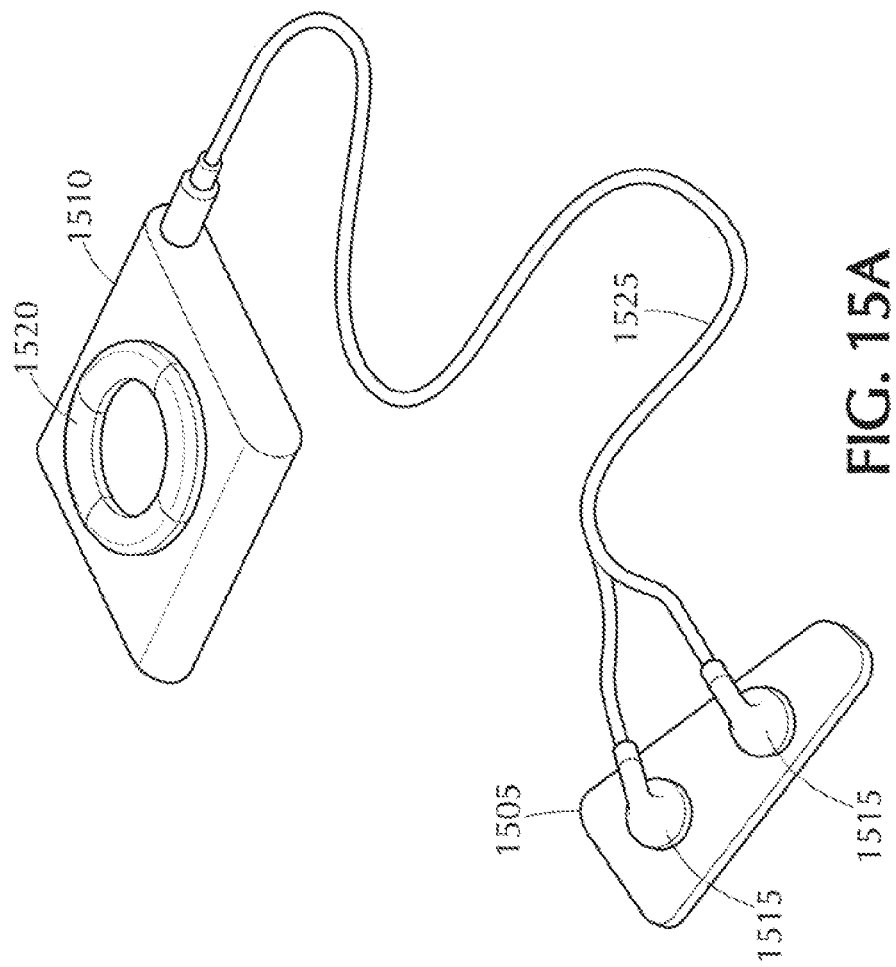
FIG. 15A shown an exemplary BAT neurostimulation system in accordance with the present invention with an external reusable control device separate from the disposable, single-use BAT transdermal electrical stimulating patch.
Figure 15B:
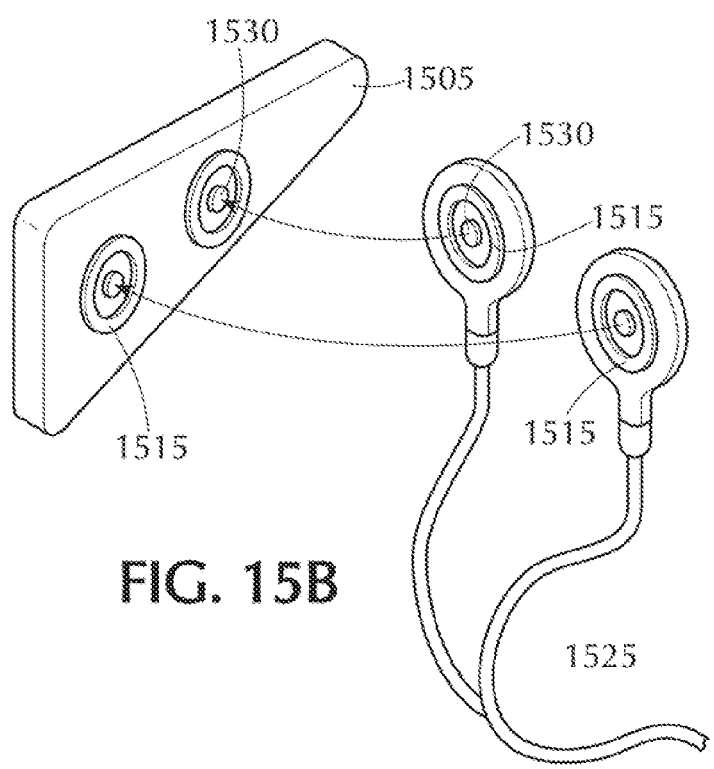
FIG. 15B shows the exemplary BAT neurostimulation system in FIG. 15A with the electric leads detached from the releasably attachable single-use BAT transdermal electrical stimulating patch.
Figures 15C, 15D, 15E:
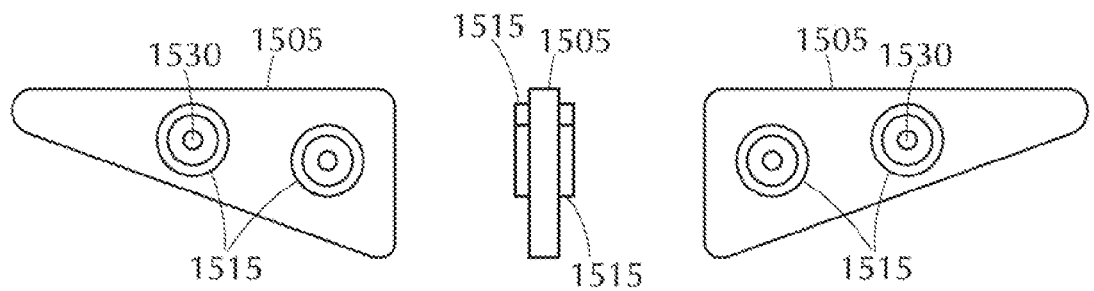
FIGS. 15C-E shows respective top, side, and bottom views of the double-sided electrode BAT transdermal electrical stimulating patch in FIG. 15A so that the same patch may be flipped over for alternate positioning on the left/right side of the body.

Patch 100 including the controller and power source may be disposable after only a single use. As an alternative, a reusable controller and power source may be separate from and releasably attached to a single-use disposable transdermal electrode stimulating patch. FIG. 15A shows an exemplary single-use disposable transdermal electrode stimulating patch 1505 connected to a reusable control device 1510 via one or more electrical leads 1525. The electrical leads 1525 are secured to the transdermal patch 1505 via a complementary releasable attachment mechanism 1515 (e.g., complementary mating snaps or opposite polarity magnets) having associated electrode contacts 1530, as seen in FIG. 15B. Depending on the level of complexity, control device 1510 may include a user interface 1520 such as one or more switches, dials, buttons, a touch screen graphical user interface; jog dial and/or any other mechanical/electrical control mechanism. The operation of control device 1510 may even be controlled by voice commands. Rather than being adhered to the skin, the reusable control device 1510 may be retained in place to an article of clothing or an accessory worn by the user using any type of releasable securing mechanism such as, but not limited to, a clip, pin; hook-and-loop (e.g., VEL-CRO®); or received within a complementary size and shape pocket sewn in the garment. The source for powering of the reusable control device 1510 may be a battery that is rechargeable or non-rechargeable. In the case of a rechargeable battery, a recharging station, base or stand may be provided. A panel in the control device provides access for replacing the battery when depleted. FIGS. 15A & 15B show a single 3-sided electrode patch 1505 complementary in size and shape to fit substantially within the supraclavicular fossa region when properly positioned on the body. The size and shape of the patch as well as the number and placement of the electrodes may be modified, as desired. As depicted in FIGS. 15C-E, the respective, front, side and back views of the patch 1505 are illustrated. It is clearly seen from these three views, that the electrode contacts 1530 are symmetrically disposed on both front and back surfaces of the patch 1505. Due to such symmetry, the patch may be alternately positioned on the right side/left side of the body merely by flipping the patch over between the front and back surfaces depending on which surface of the patch is to be applied to the body. More than one patch may be applied on one or both sides of the body.

Figure 16A:
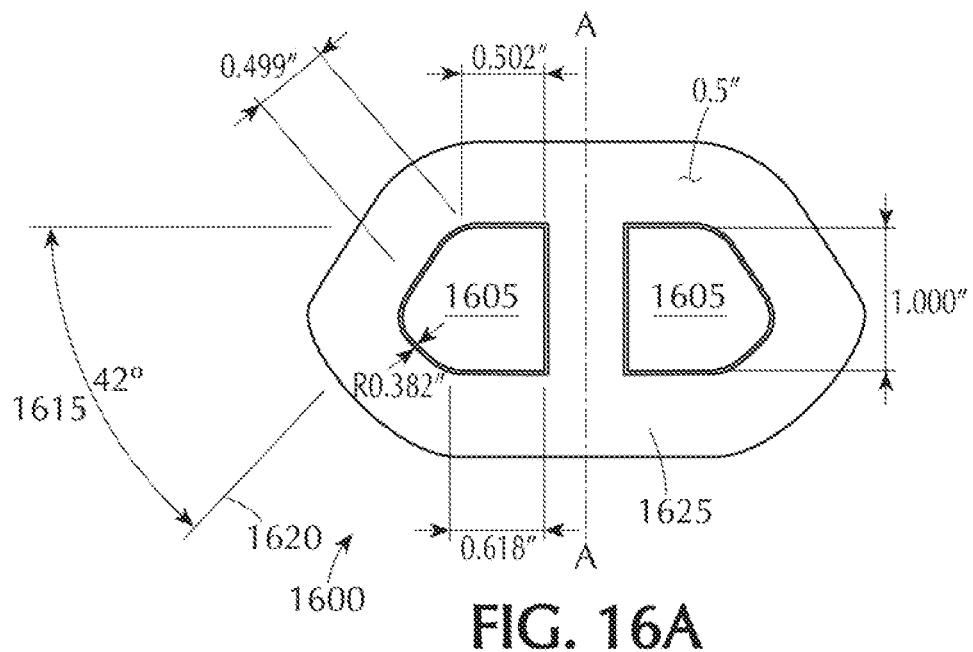
FIG. 16A is a bottom view of an exemplary BAT transdermal electrical stimulating patch in accordance with the present invention wherein the electrodes are symmetrically arranged on a single side so that the patch may be placed on the right/left of both sides of the body at least partially in the supraclavicular fossa.
Figure 16B:
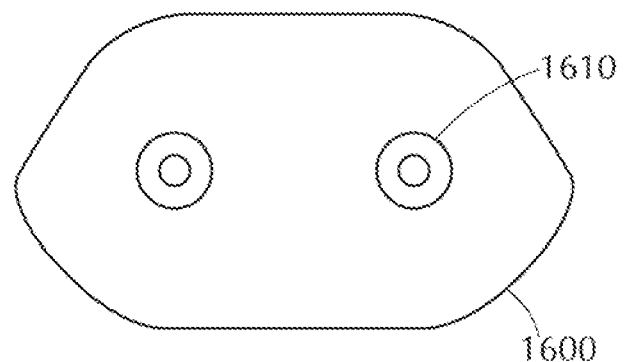
FIG. 16B is a top view of the exemplary BAT transdermal electrical stimulating patch of FIG. 16A.
Figure 16C:
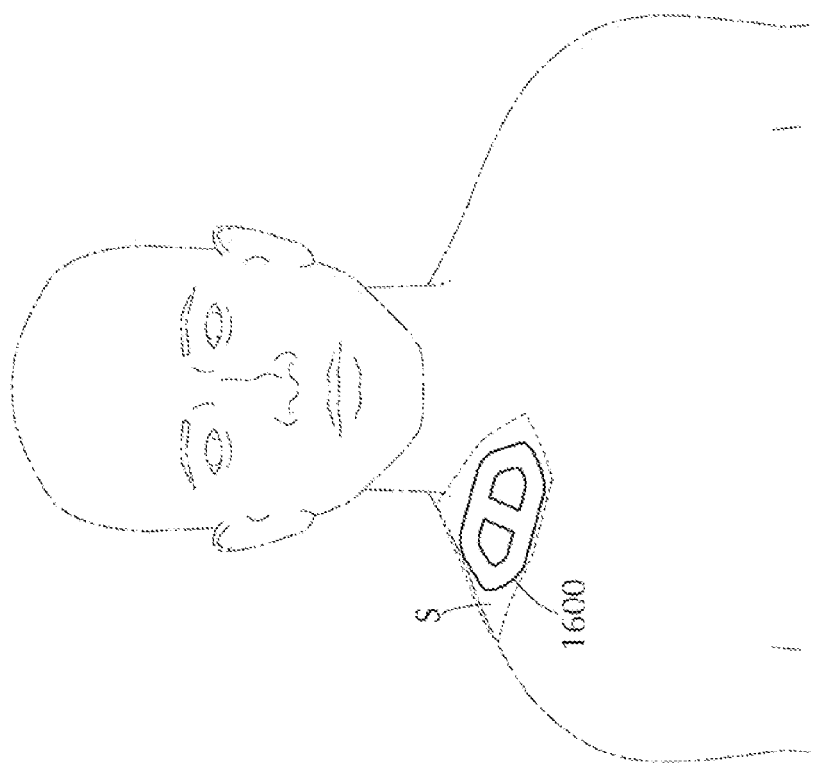
FIG. 16C illustrates the patch in FIG. 16A positioned within the supraclavicular region of the body as shown in FIG. 14.

Even in the embodiment in which the electrodes are disposed only on one surface of the patch, they nevertheless may be configured symmetrically with respect to an imaginary axis dividing the patch into two sections. FIGS. 16A and 16B depict such an exemplary patch 1600 in accordance with the present invention in which the electrodes 1605 are disposed on a single surface and arranged symmetric with respect to the axis A-A so that the patch may be placed on the right/left sides of the body entirely within the supraclavicular fossa area by simply reorienting or rotating the patch without flipping it over. Snap on leads may be disposed on its opposite surface, as depicted in FIG. 16B, so that electrical leads may be readily attached to/removed from the patch. The size and shape of the patch in FIG. 16A is such that it fits within the supraclavicular fossa area "S," shown in FIG. 14. Referring to FIG. 16C, in which the patch 1600 is positioned on a single side of the body within the triangular supraclavicular fossa region "S", electrode 1605 has been designed to include an angled or tapered region 1615 for clearance of the trapezius muscle, while the curved region 1620 maximizes the power delivery while simultaneously preventing unsafe current levels. Both electrodes 1605 are encircled ay an adhesive film 1625 to releaseably adhere the patch to the skin when properly positioned within the supraclavicular fossa region of the body. The measurements depicted in FIG. 16A are for illustrative purposed only and not intended to limit in scope the present invention.

After remaining in the same position on the skin for a predetermined period of time an adhesive skin patch will irritate or possibly even damage the skin on which it is adhered. To minimize or prohibit skin irritation or damage, the location in which the adhesive associated with the patch is adhered to the skin is periodically moved to a new or different position on the body. Such repositioning may take place preferably approximately every 3 to 11 days, most preferably approximately every 7 days. Considering such frequency, it is impractical to require the user to visit a doctor, nurse or technician to have a new patch applied to a new location on the body. Accordingly, the present invention contemplates various methodology and techniques to assist the user in correctly self-applying the transdermal electrical stimulation patch to activate BAT depot in the supraclavicular fossa region of the body without the need for an office visit or assistance from any other individual. Simplicity of use will significantly improve patient compliance so minimum instruction is preferred. In keeping with these factors, the patch design is also preferably relatively inexpensive to manufacture and requires no calibration. Accuracy in placement of the stimulation device with each repeated use insures compliance and consistency of treatment.

When configuring the transdermal electrical stimulating patch all components including one or more electrodes, electronics and a power source are preferably located within the supraclavicular fossa region when properly positioned on the body. Alternatively, the patch may be configured so that when properly positioned on the body at least one electrode lay within the supraclavicular fossa region of the body, while some of the electrodes, some of the electronics, the power source or some combination thereof may lay outside (e.g., above or below) the supraclavicular fossa region. A particular patch configuration or design may be influenced, at least in part, by the location of the one or more electrodes, electronics and/or the power source.

When designing the patch, competing factors play a roll. On the one hand, it is desirable to minimize the size of the footprint making the patch as inconspicuous as possible by incorporating all components into the patch so that it is contained entirely within the targeted BAT depot (e.g., supraclavicular fossa region BAT depot); while, on the other hand, the size of the battery and other electronic components often exceed in size that of the targeted BAT depot (e.g., supraclavicular fossa region BAT depot). To accommodate such competing factors, the patch may be configured, as desired, so that when properly positioned on the body one or more of the following components lay outside the supraclavicular fossa region: (i) power source; and (ii) some or all of the electronic components (possibly including one or more electrodes).

Figure 3:
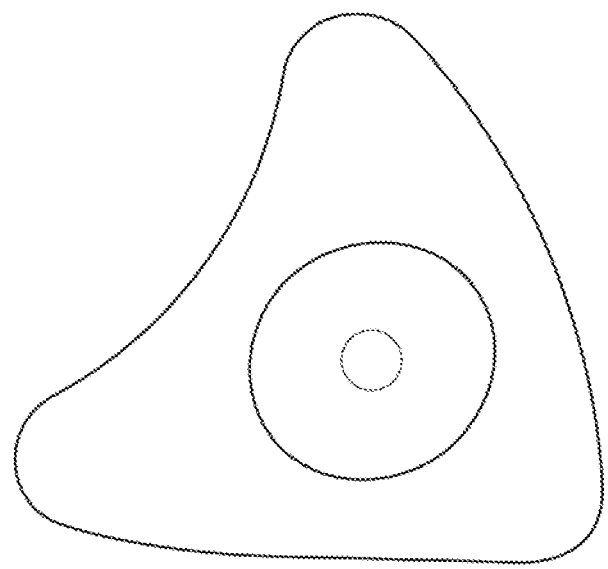
FIG. 3 is still another exemplary configuration of the BAT activation transdermal electrical stimulating patch in accordance with the present invention.

When one embodiment of the patch depicted in FIG. 3 is properly positioned on the body, all electrodes, electronic circuitry and the power source is contained within the supraclavicular fossa region in order to activate the target BAT volume therein. In an alternate configuration, some of the electrodes, some of the electronic, the power source or some combination thereof may lay outside the supraclavicular fossa regions when positioned on the body, as discussed in detail below.

Figure 2B:
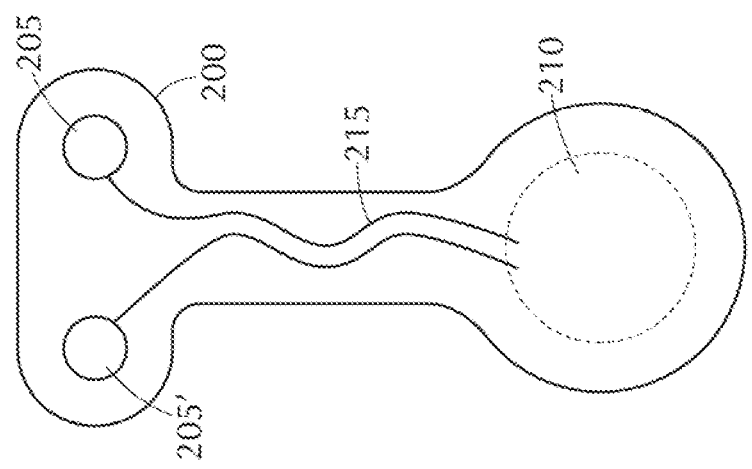
FIG. 2B is another exemplary configuration of the BAT activation transdermal electrical stimulating patch in accordance with the present invention, wherein when properly positioned on the body, both electrodes are disposed within the supraclavicular fossa region.
Figure 2A:
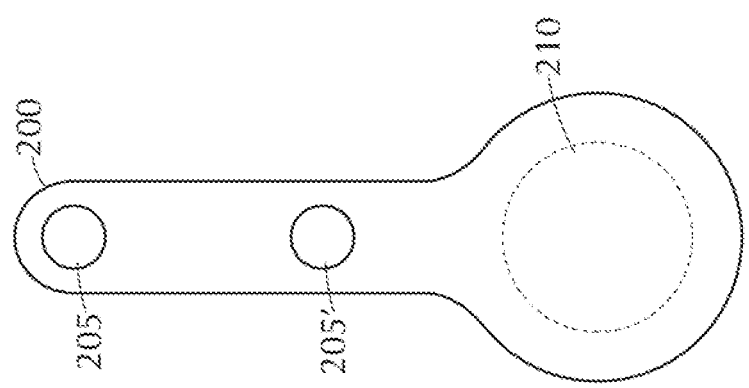
FIG. 2A is an exemplary configuration of the BAT activation transdermal electrical stimulating patch in accordance with the present invention, wherein when properly positioned on the body, one electrode is disposed within the supraclavicular fossa, while the other electrode is located outside the supraclavicular fossa.

FIGS. 2A and 2B depict an exemplary configuration of a transdermal electrical stimulating patch 200 having two electrodes 205, 205' for generating an electric field to activate BAT depot in the supraclavicular fossa region. When properly positioned on the body, one electrode 205 in FIG. 2A lay within the supraclavicular fossa region, while a second electrode 205' lay outside the supraclavicular fossa region. With the alternative configuration in FIG. 2B, when the patch is properly positioned on the body, both electrodes 205, 205' are disposed within the supraclavicular fossa region while the power source 210 connected via electrical paths 215 to the respective electrodes 205, 205' lay outside the supraclavicular fossa region. Independent electrical paths may be provided between each of the electrodes and the controller, as represented by the U-shaped patch with two electrodes 205 in FIG. 2G, while FIG. 2H depicts an exemplary patch configuration in which the electrodes 205 share a common electrical path.

Different patch configurations are possible for activation of the BAT depot in the supraclavicular fossa region. At one end of the spectrum, all components (e.g., all electrodes, all electronics and the power source) lay within the supraclavicular fossa region, when the patch is properly positioned on the body. While at the other end of the spectrum, all of the components (e.g., one or more other electrodes, electronics and/or the power source) are disposed outside the supraclavicular fossa region. Between these two extremes, an infinite number of combinations are possible in which some, but not all, of the electrodes, electronics, power source or some combination thereof lay within the supraclavicular fossa region, while the remaining components lay outside this region. The size and shape of the electric field generated by the patch may be modified to cover the target BAT volume by changing the number and/or arrangement of the electrodes.

Figure 2D:
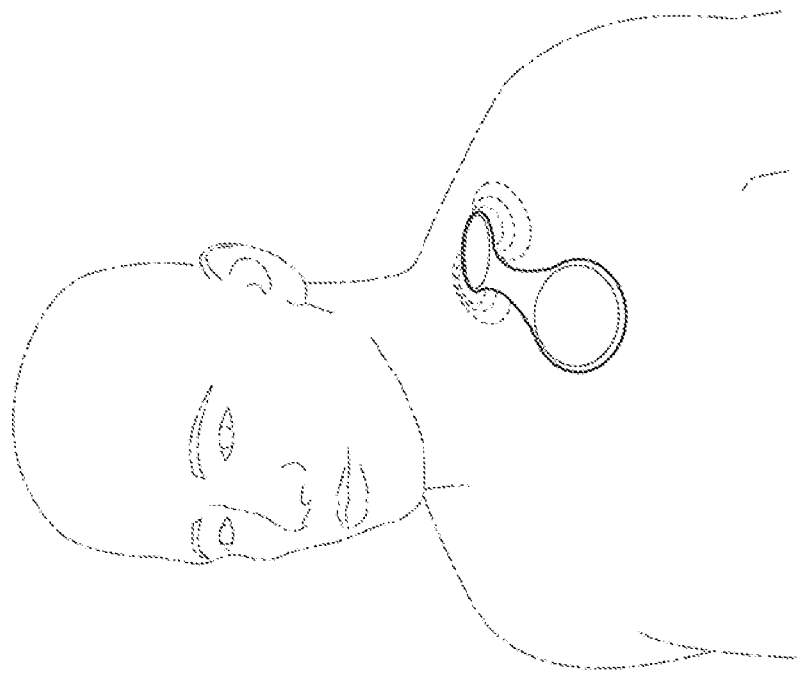
FIGS. 2C & 2D illustrate the patch similar in shape to that in FIG. 2A disposed on the respective right and left sides of the body.
Figure 2C:
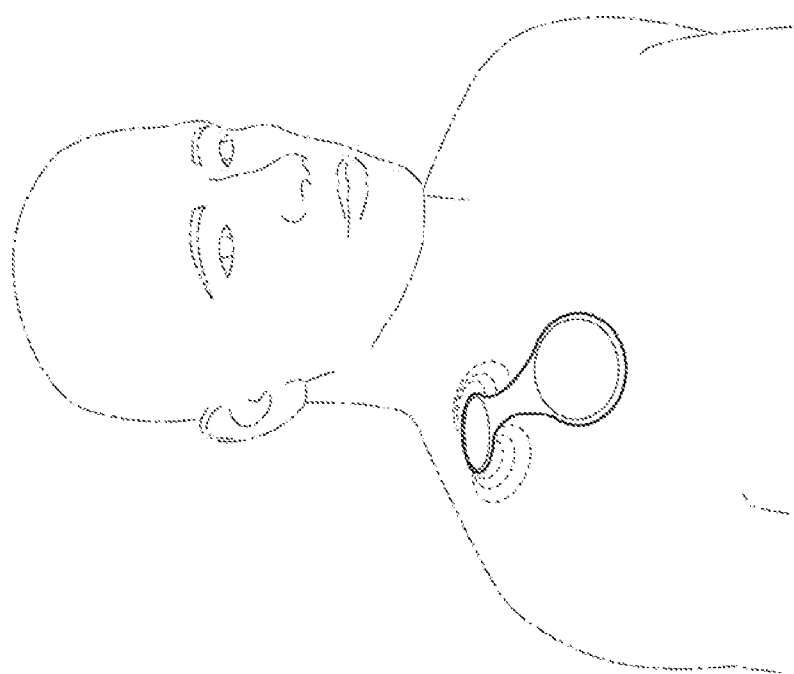
Figure 2F:
FIGS. 2E & 2F are respective back and side views of the patch similar in shape to that in FIG. 2A adhered to the right side of the body.
Figure 2E:
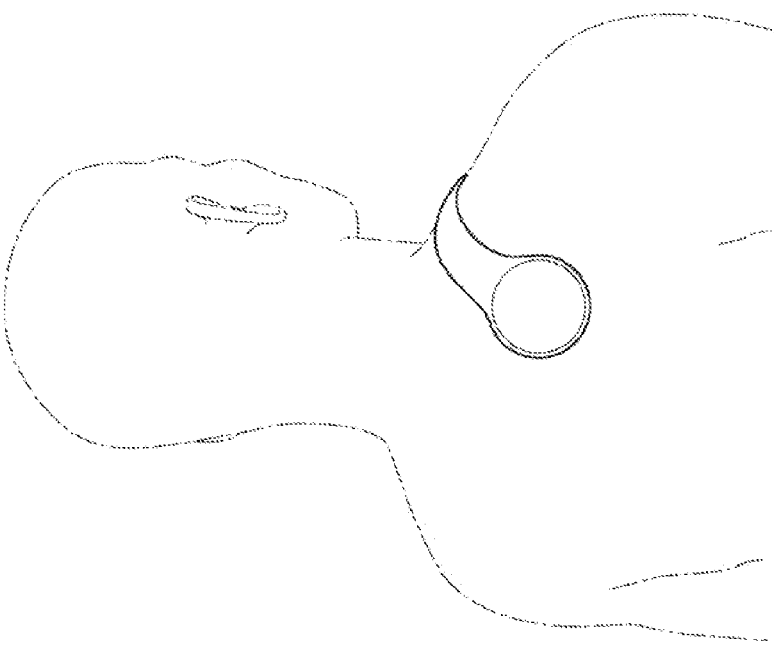

When a portion of the patch lay outside the supraclavicular fossa region, the patch may straddle the clavicle or extend front-to-back over the shoulder. Referring to FIGS. 2C and 2D, this exemplary patch is adhered entirely to the chest straddling the clavicle with at least one electrode disposed above the clavicle within the supraclavicular fossa region while the electronic control circuitry and power source are positioned below the clavicle. To minimize skin irritation, placement of the patch may alternate between the right and left sides of the body, as depicted in FIGS. 2C and 2D, respectively. Instead of being contained entirely on the chest, the patch may be oriented front-to-back straddling the shoulder, as depicted in FIGS. 2E & 2F. In this alternative placement, once again the stimulation area of the patch, including one or more electrodes, is positioned within the supraclavicular fossa region of the body while the electronic control circuitry and power source (e.g., battery) is adhered on the back with electrical leads or paths connecting the circuitry therebetween. Preferably a releasable adhesive is provided at least about the perimeter of the stimulation area, electronic control circuitry and power supply. With this configuration, the power source, which typically is the electronic component in the patch exhibiting the highest side relief profile, is preferably disposed on the back making the device less conspicuous. Once again placement over the shoulder allows alternate positioning on the left/right side of the body to minimize skin irritation. With all embodiments the overall aesthetic design of the patch may be made fashionable and/or as inconspicuous as possible.

Referring once again to the exemplary transdermal electrical stimulation patch depicted in FIGS. 2C and 2D, all electrodes are adhered to the chest in substantially the same plane. It is contemplated that the electrodes may be located in more than one or different planes to generate an electric field having a particular size, shape and contour reflecting the anatomy and, in particular, such physical structures as (e.g. bone, muscle, skin and/or fat densities). For instance, an electric field signal may be generated using electrodes that lay in different planes in order to bathe and thereby excite the greatest volume of nerves attached to the BAT cells. In the illustrative example depicted in FIGS. 13A & 13B, one or more electrodes 1305 are disposed within the surpraclavicular fossa region, while one or more other electrodes 1310 lay outside the supraclavicular fossa region (e.g., on the shoulder). Since electrode 1310 is positioned on the shoulder it is located in a different plane (plane B) then the plane (plane A) of electrode 1305 positioned on the chest in the supraclavicular fossa region. That is, the two electrodes 1305, 1310 when positioned on the body need not lie within the same plane. This may be the case when the patch is configured such that one or more electrodes, some or all of the electronics and/or the power source is positioned outside the supraclavicular fossa region (e.g., below the clavicle or on the back) so as to generate an electric field of a particular shape and area to target a desired BAT volume.

Activation of the target BAT volume in the supraclavicular fossa region requires proper positioning of the patch and the electrodes associated therewith. Placement of the patch by the user without requiring assistance from any other individual is a significant design factor. One or more anatomical landmarks (representing a two-dimensional anatomical reference such as the intersection of two bones, e.g., clavicular junction with the sternum) and/or anatomical features (representing a three dimensional anatomical reference, e.g., clavicle, chin, sternum, trapezius and/or neck) may be used as a reference point(s) or guide to properly position the patch prior to adhering it to the body. This can be achieved by a portion of the patch keying off one or more anatomical features and/or anatomical landmarks. Instead of an integrated design, a bifurcated or two-part patch configuration may be utilized wherein a first portion of the patch serves merely as a template or frame, while a second portion includes one or more electrodes for producing an electric field used to stimulate the BAT beneath the skin. The second portion of the patch is properly positioned on the body using the first portion of the patch as a reference or a guide.

Figure 4A:
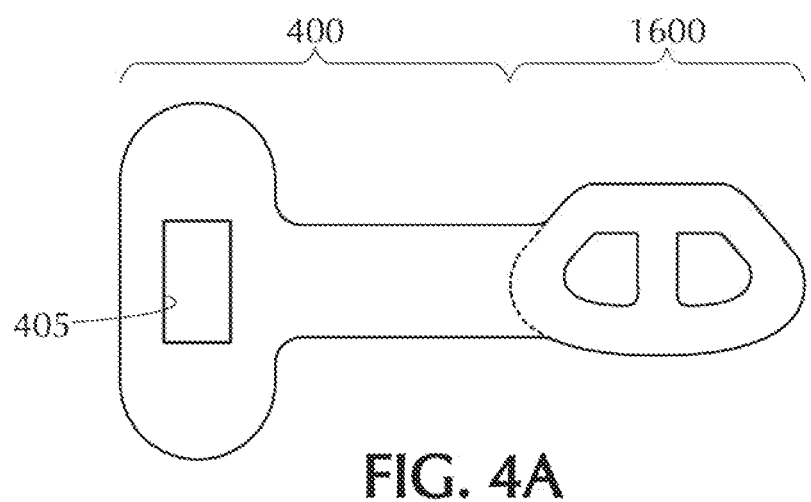
FIG. 4A is another exemplary configuration of a bifurcated BAT activation transdermal electrical stimulating patch in accordance with the present invention, wherein a first portion of the patch serves as a template with a keyhole defined therein to be aligned with an anatomical placement sticker properly positioned on the body, whereas the second portion of the patch provides electrode stimulation.

FIG. 4A shows an exemplary bifurcated patch including template or frame section 400 and electrode stimulation section 1600 (as shown in FIGS. 16A & 16B) separable from one another. A cutout, transparent window, keyhole or opening 405 defined in the template section 400 is substantially aligned with an anatomical reference placement sticker 402 positioned relative to a feature/landmark of the body defined by the sternum, right clavicle, the left clavicle or some combination thereof. Proper positioning of at least one electrode within the supraclavicular fossa region of the body in order to activate the BAT therein is insured by first positioning the anatomical reference placement sticker 402 so that it is substantially aligned with a recess of the body defined by the sternum, right clavicle and left clavicle. Thereafter, the cutout, transparent window, keyhole or opening 405 defined in the template section 400 of the bifurcated patch is substantially aligned with the anatomical reference placement sticker 402. Once the patch has been properly positioned, the anatomical reference placement sticker 402 and template section 400 of the patch may be removed, leaving the electrode stimulation section 1600 of the patch adhered to the body properly positioned to stimulate the BAT in the supraclavicular fossa region. It is noted that one or more different anatomical features and/or anatomical landmarks may be used with the number, size and shape of the cutouts, transparent windows, keyholes or openings defined in the patch dictated by those one or more anatomical features and/or landmarks being referenced. Preferably, the patch design for the template section is such that it may be used irrespective of positioning of the electrode stimulation section 1600 on the left/right side of the body. Furthermore, the placement sticker may be eliminated altogether and the cutout, transparent window, keyhole or opening 405 defined in the template section 400 substantially aligned with the anatomical landmark/feature itself.

Figure 12A:
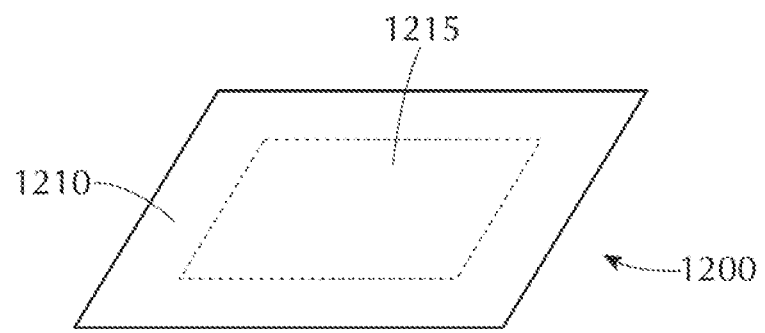
FIG. 12A shows an exemplary placement template preloaded with the BAT transdermal electrical stimulating patch.
Figure 12B:
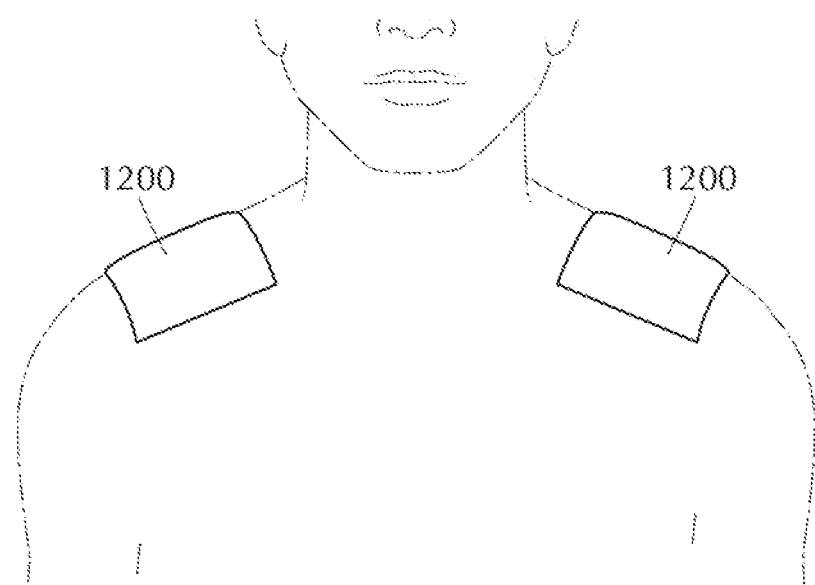
FIG. 12B illustrates the placement template with preloaded BAT transdermal electrical stimulating patch properly positioned on the body.

Another exemplary bifurcated patch configuration is shown in FIGS. 12A and 12B in which the first portion of the patch is a template or frame 1210 that is rectangular or square in shape with a similarly shaped smaller size opening, keyhole or cutout defined therein. A complementary size and shape second portion electrode patch 1215 is preloaded in the opening, keyhole or cutout. One corner of the template or frame first portion 1210 of the patch is positioned at the end of the clavicle closest to the shoulder. Advancing towards the sternum the bottom edge of the template or frame first patch portion is substantially aligned along the length of the clavicle. Thereafter, the template or frame first patch portion 1210 having fulfilled its intended purpose is removed from the skin leaving in place the properly positioned second portion electrode stimulation section 1215 adhered to the body. Because the shape of the template or frame portion 1210 of the patch shown in FIG. 12A is symmetric it may be used for properly positioning the second portion electrode stimulation section 1215 of the patch on the left/right side of the body. The use of either an integrated or bifurcated patch has several advantageous features including, but not limited to: minimal cost of manufacture, minimum storage requirements, portability and disposable after only a single use or application. The number of portions as well as the particular shape and size of each portion of the multi-portion patch may be modified, as desired, depending on such factors as the one or more anatomical landmarks and/or anatomical features to be used as a reference when properly positioning the template portion of the patch as well as the size and shape of the target area being stimulated. Furthermore, rather than a single patch as the second portion electrode stimulation portion 1215, a plurality of patches nested within the template 1210 and decreasing in size may be provided.

Figure 5C:
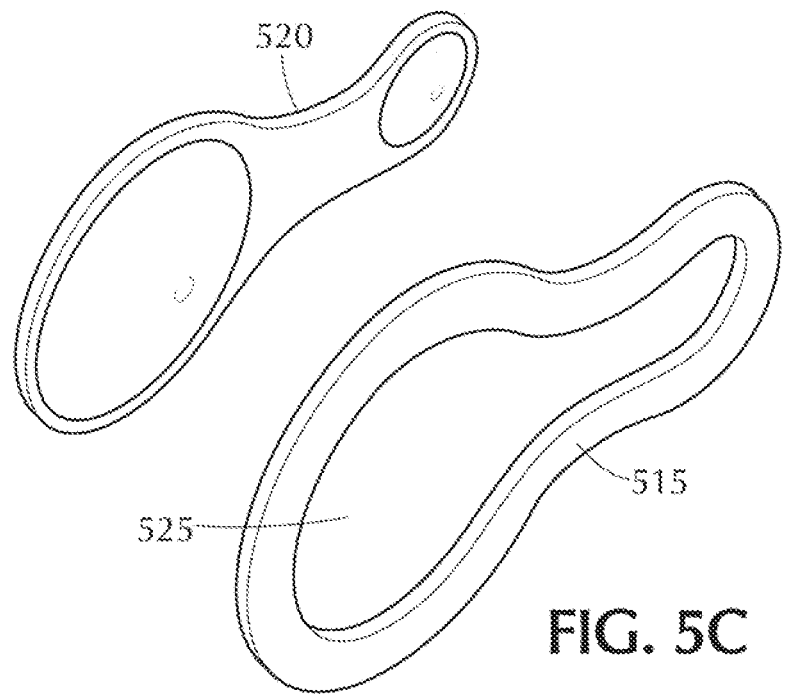
FIGS. 5C and 5D are exemplary configurations of different frame templates in the mechanical device of FIG. 5A.

A separate reusable mechanical placement tool may be utilized in properly positioning the transdermal electrical stimulation patch. The reusable mechanical placement tool references one or more anatomical landmarks and/or anatomical features. In FIGS. 5A & 5B, two anatomical features, e.g., the chin and the sternum, provide the reference points or datum. Mechanical placement tool 500 includes a stationary arm 505 and a rotatable or pivoting arm 510. The stationary arm 505 is sized and shaped so that one end ergonomically fits under the chin while the opposite end is contoured to rest atop the sternum. Once the stationary arm 505 has been properly positioned between the chin and sternum, arm 510 is rotated toward the body until a template or frame patch 515 (FIG. 5C) with its adhesive side exposed outwardly from its free end contacts the body thereby automatically adhering it at the proper location to activate BAT disposed within the supraclavicular fossa region. The reusable mechanical locator tool preferably pivots to the right and to the left to place the template or frame patch on the right/left or both sides of the body. If not, two separate mechanical locator tools may be provided, e.g., one that pivots only to the right, while the other pivots only to the left. Mechanical locator tool 500 is preferably adjustable longitudinally to accommodate each individual user. Such personalized customization may be realized by using telescoping parts, rotation, spacers or other mechanical/electrical adjustment mechanisms.

Figure 5D:
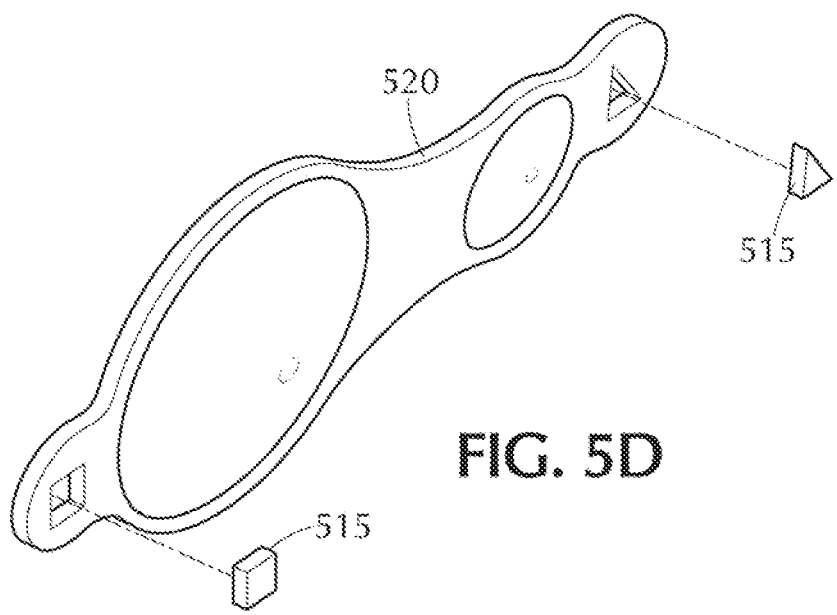

Once the template or frame patch 515 is adhered to the body in the proper position, the mechanical locating tool 500 is removed and the electrode patch 520 is positioned relative to the template or frame patch 515. For instance, electrode patch 520 may be positioned within a cutout or opening 525 defined in the template or frame patch 515 that is sized and shaped to receive it. Alternatively, the electrode patch 520 may be preloaded together with the template patch 515, prior to being loaded in the mechanical locating tool 500. After the electrode patch 520 has been adhered to the body in its proper position to activate BAT within the supraclavicular fossa region of the body, thereafter the template or frame patch 515 may be removed from the body leaving, in place the properly positioned electrode patch. FIGS. 5C & D depict alternative configurations in which the electrode patch 520 is aligned relative to one or more frame or template patches 515. Specifically, in FIG. 5C frame or template patch 515 has an opening or cutout 525 defined therein complementary in size and shape to receive electrode patch 520. Whereas in FIG. 5D, two frame or template patches (one square in shape, the other triangular in shape) are of a size and shape to be received within complementary defined openings or cutouts in the electrode patch 520. Once again, the size, shape and number of frame or template patches may be modified, as desired, with this bifurcated or two-part design.

Figure 11A:
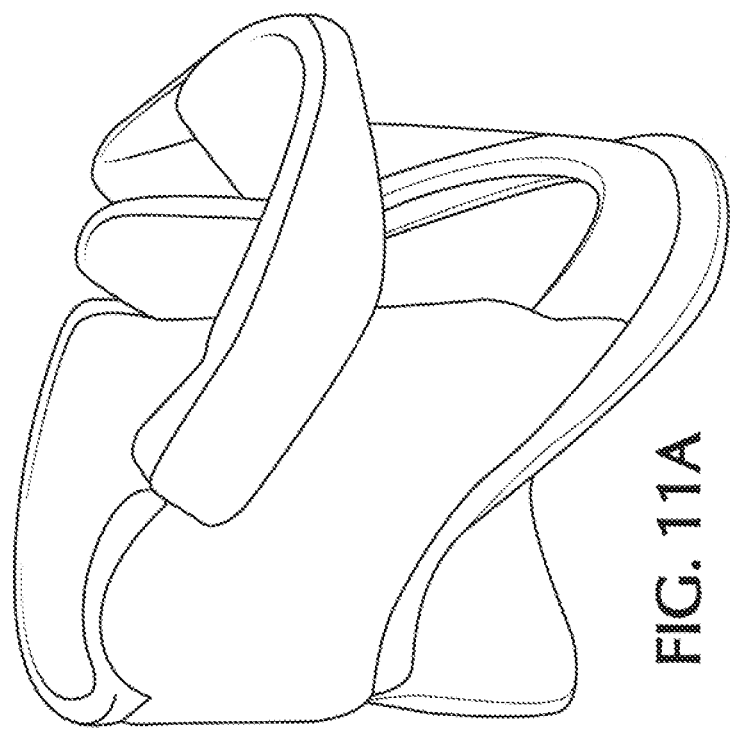
FIG. 11A is an exemplary device for proper positioning of at least a portion of the BAT transdermal electrical stimulating device in the supraclavicular fossa using the neck and/or shoulders as anatomical features.
Figure 11C:
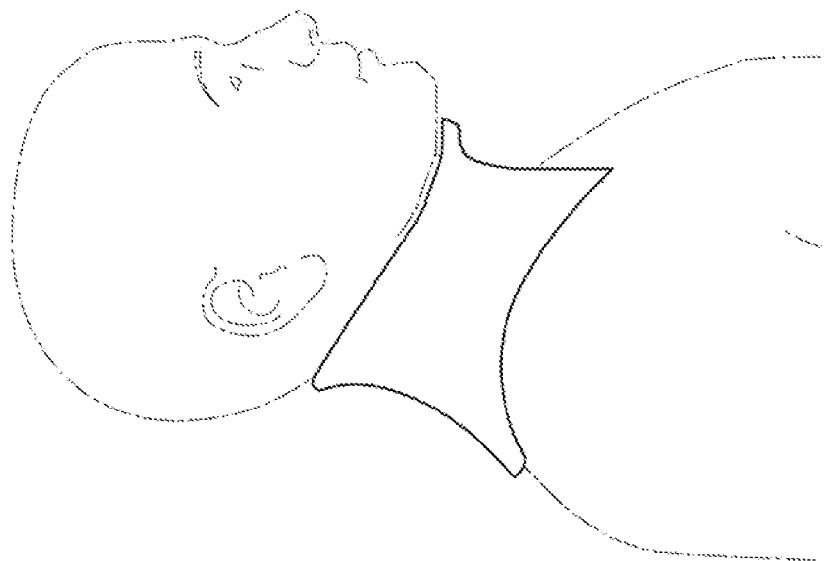
FIGS. 11B & 11C are respective front and side views of the positioning device in FIG. 11A worn on the body.
Figure 11B:
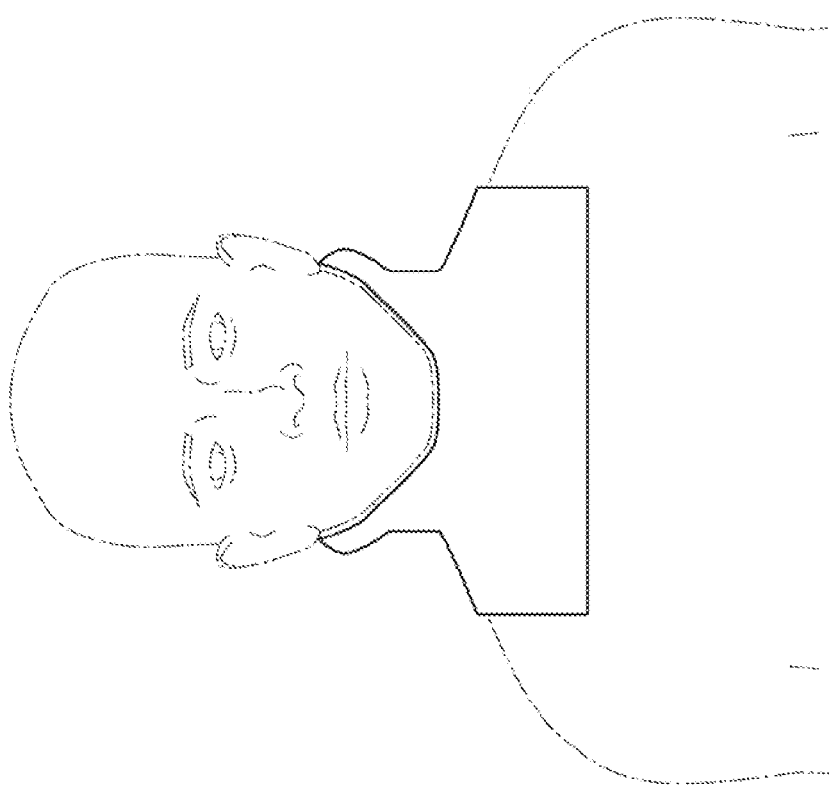

Yet another separate mechanical placement tool for the electrode patch is a neck-shoulder physical device or template that is placed around the neck and rests on the user's shoulders similar to that of a neck brace with shoulder pads, as depicted in FIGS. 11A-11C. One or more openings are defined in the shoulder pad area, each opening complementary in size and shape to receive therein the electrode patch. Preferably, the mechanical placement tool is supported by the shoulders while being positioned about the neck. Once secured about the neck and resting on the shoulders, thereafter the electrode patch is received in an opening defined in the mechanical placement tool whereby the adhesive backing upon contacting with the skin secures it in place on the body. Finally, the mechanical placement tool is removed, leaving in place the electrode patch properly positioned at least partially within the supraclavicular fossa region of the body. The neck-shoulder mechanical placement tool preferably has two symmetric openings defined in the respective shoulder pads for placement of the patch on the left/right side of the body.

Rather than a mechanical placement tool or device, one or more reference points may be marked or tattooed using a dye or ink with minimal presence on the user's body to properly position the transdermal electrical stimulation patch for activating BAT within the supraclavicular fossa region of the body. In order to remain inconspicuous to others, the size of the mark is preferably as small as possible, yet still visible to the user. For example, the tattoo marking may be as small as approximately 0.1 inch. By way of example, the mark may be an "X", dot, circle, "+" sign or any other desired shape regardless how complex or simple. Due to their shape, some marks, such as a "+" sign, establish a two dimensional X-Y coordinate reference system thus requiring only a single marking. In contrast, a dot typically requires more than one mark to fix position and/or rotation. For example, three dots may be positioned substantially equidistant proximate a perimeter of the patch. In keeping with the desire to remain as inconspicuous as possible, the dye or ink used for the tattoo or marking is preferably outside the visible spectrum. For instance, ultraviolet ink or dye may be used which is visible only in the presence of black light. The ink or dye may be permanent or temporary. In the case of a temporary ink or dye the timing of its disappearance may be coordinated with the timing of a follow-up visit to a physician or technician.

Figure 6:
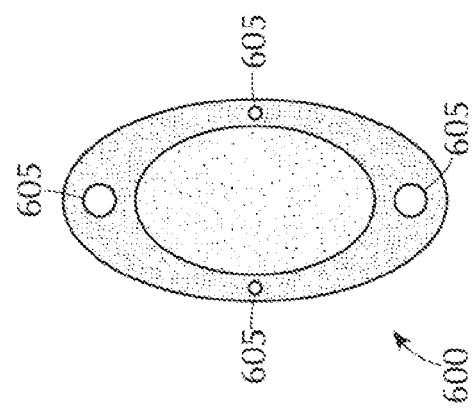
FIG. 6 is an exemplary BAT activation transdermal electrical stimulating patch in accordance with the present invention including one or more openings through which markings on the body may be viewed and aligned to insure proper positioning of the patch to activate BAT depot in the supraclavicular fossa area.

A corresponding number of reference location transparent windows, keyholes, openings or cutouts are provided in the transdermal electrical stimulation patch so that when properly aligned over the body the markings or tattooed indicia are visible therethrough confirming its correct placement on the body. FIG. 6 is a representative example of the electrical stimulation patch 600 having four windows 605 to be aligned with corresponding tattoo markings on the user's body. If ultraviolet (UV) ink or dye is used for the tattoo markings then either an internal black light source associated with or separate from the patch itself may be used to illuminate the markings through the transparent/translucent windows or cutouts. The windows or cutouts defined in the patch insure the correct orientation and placement of the patch on the body. Tattoo markings advantageously allow for repeated alignment with the patch over a relatively long period of time, e.g., one or more years, without the need for reapplication. As with all other embodiments, the tattoo markings are preferably made on both the right and left sides of the body to allow for alternate placement of the patch on one or both sides of the body. The number, placement, shape, size, etc. of the tattoo markings may be modified, as desired.

Figure 8:
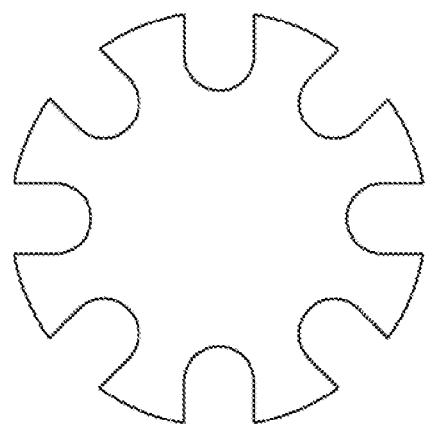
FIG. 8 is an exemplary adhesive pad template clock with eight equidistantly arranged notches defined about its perimeter.
Figure 9A:
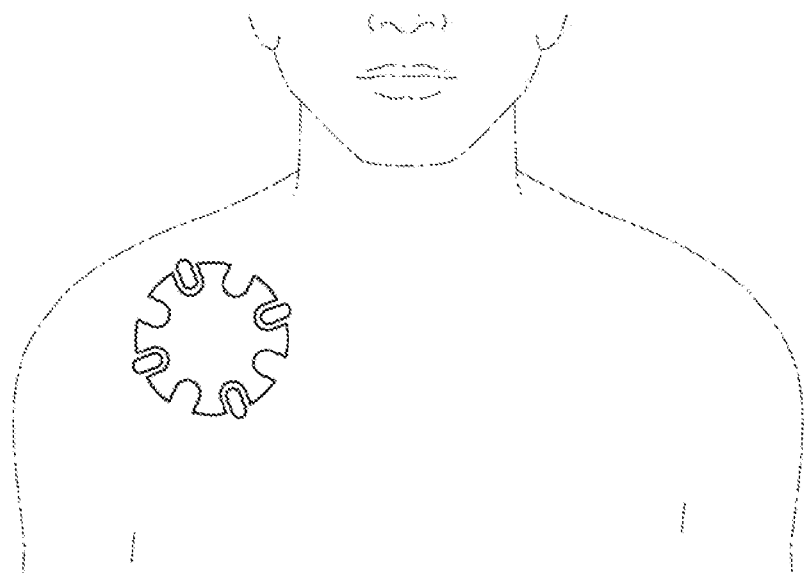
FIGS. 9A & 9B depict illustrative first and second week pad adhesive locations, respectively, rotated by approximately 45 degrees relative to one another.
Figure 9B:
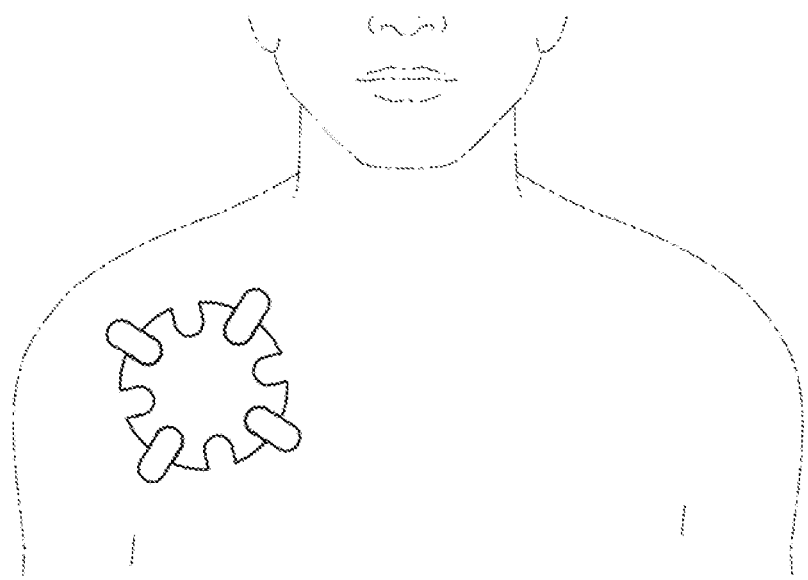

As previously noted temporary skin irritation or worse, permanent damage, resulting from the adhesive patch is of significant concern. In the preceding embodiments such as that shown in FIGS. 2A, 2B and 3 adhesive is disposed about the perimeter of the patch to adhere to the skin of the user's body. The relatively large surface area of the adhesive dictates a symmetrical approach in which the position of the patch alternates between left/right sides of the body. Instead, it is possible for the patch to remain positioned on the same side of the body and merely change the location or orientation of one or more adhesive pads or offset circumferential adhesive rings that secure the patch to the body. In so doing, the adhesive on the patch is significantly reduced in size to discrete pads so that when the orientation of the patch is changed, the adhesive may be placed in different locations on the skin. In particular, a plurality of discrete adhesive pads are positioned at a first orientation or arrangement about the perimeter of the patch. The following week, the position of the patch itself on the body remains unchanged, however, the adhesive pads are removed from the first arrangement and positioned at a second arrangement, different from the first arrangement, proximate the perimeter of the patch. Thereafter, on the third week, the adhesive pads may be returned to the first location or orientation. Either new adhesive pads may be applied or the same adhesive pads may be reused, so long as they remain substantially intact and retain their adhesiveness. Instead of changing the position of the adhesive pads relative to the patch, the orientation of the patch itself may be rotated a predetermined number of degrees while remaining at a substantially fixed location on the body so that the adhesive pads are positioned at a different location on the body. To assist in placement of the adhesive pads at the first and second orientations, a template may be used, such as that depicted in FIG. 8, with eight equidistantly spaced notches defined about the perimeter representing the location of the adhesive pads in both the first and second orientations. In accordance with the example in FIG. 8, on the first week the four adhesive pads are positioned at a first orientation along the perimeter of the patch approximately 90 degrees apart from one another (FIG. 9A). After the first week a template (such as that shown in FIG. 8) is positioned over the patch, the adhesive pads are released from the skin and the patch is rotated approximately 45 degrees in either a clockwise or counterclockwise direction to relocate the position of the pads (FIG. 9B). If the adhesive pads remain substantially intact and retain their adhesiveness they may be reused in their new location, otherwise, new adhesive pads or a complete adhesive component may be used once the old ones have been removed.

Figure 10A:
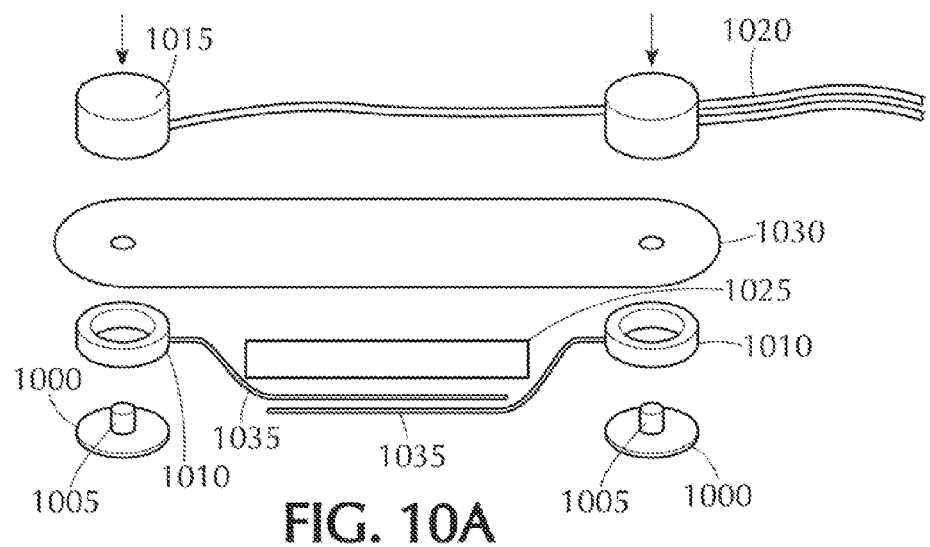
FIG. 10A diagrammatically depicts an exploded view of the exemplary snap-on patch.
Figure 10B:
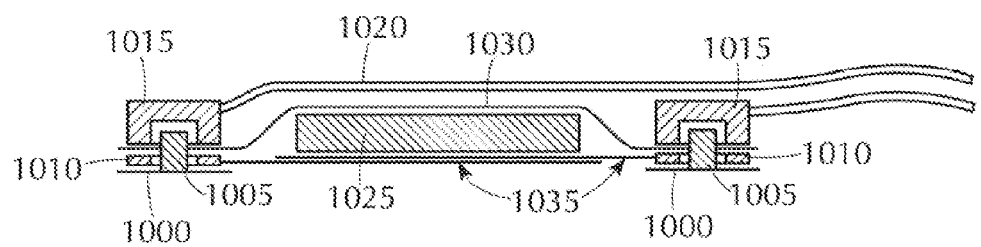
FIG. 10B depicts a cross-section view of the assembled snap-on patch of FIG. 10A.

The number of adhesive pads and their location relative to the patch may be varied, as desired. Notches defined in the template are dictated, at least in part, based on the number and arrangement of the adhesive pads. Despite the relocation of the adhesive pad positions from week-to-week, the position of the transdermal electric stimulation patch remains substantially unchanged. In a modification of this embodiment as shown in FIGS. 10A & 10B, one or more adhesive pads 1000 may have affixed to its top surface a button or other protrusion 1005. The "snap-on" patch, in turn, has a complementary shaped disc or recess 1010. Together mating button 1005 and recess 1010 form a securing mechanism for electrically connecting the snap on electrical connectors 1015 to the electrical leads or wires 1020 with a covering 1030 therebetween. The releasability of the securing mechanism allows for temporary removal of the patch, for example, while showering, while leaving in place the adhesive pads. Once the skin has been cleaned and dried, the patch may be readily secured into position. Movement of the user's arms or other parts of the body may result in folding, creasing or bunching of the electrode possibly interrupting stimulation of the BAT as well as being uncomfortable to the wearer. To enhance comfort while simultaneously insuring conductivity between electrode layers 1035 and the skin over a range of motion, a conformal material (e.g., hydrogel layer, foam or any other material that exerts pressure onto the electrode surface) 1025 is disposed between the electrode layers 1020 and the protective covering 1030. By way of illustrative example, the thickness of the hydrogel layer may be approximately 0.025" or approximately 0.040." The thicker the hydrogel layer the more forgiving of wrinkles, creases or non-linear skin surface movement.

Figure 7:
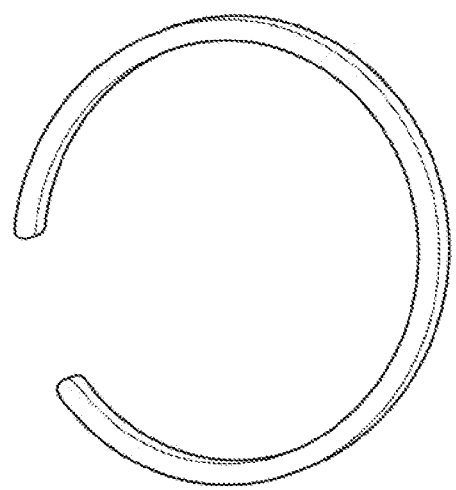
FIG. 7 is a partially implanted body piercing ring as a dual purpose location reference and electrode to which an electrical waveform signal is applied to activate BAT in the supraclavicular fossa region.

A body piercing with an object inserted partially into the body may also be used as an integrated placement tool and electrode. An added advantage of a body piercing, aside from its reuse for many years, is that since the object itself is partially inserted or implanted into the body it may be instrumental in delivery of the electrical field to activate the BAT in the supraclavicular fossa area. Furthermore, the use of a body piercing may eliminate the need for adhesive otherwise associated with a transdermal patch that over time undesirably irritates the skin. FIG. 7 is a small metal ring object body piercing, preferably approximately one or more tenths of an inch, positioned within the supraclavicular fossa region of the body. The body piercing object may be made of a conductive material such as 316L stainless steel, titanium, gold plated, etc. A clamp, snap, magnet or any other releasably attachable mechanical device may be used to connect the electronics via an electrical lead to the object body piercing and electrically stimulate the BAT beneath the skin. The object body piercing delivers the electrical stimulation waveform signal to the BAT proximate where the piecing penetrates the skin. To prevent skin irritation and/or to shape the electrical field, the object body piercing may be at least partially insulated at least where the piercing penetrates the skin. Materials used to insulate the object body piercing include, but are not limited to, Kynar™, fluorinated ethylene propylene (FEP), parylene or other polymer. This particular embodiment is advantageous in that it remains in place for an extended period of time and yet body piercings are a commonly accepted form of body jewelry that would draw minimal attention. The shape and size of the object body piercing may be adapted, as desired, to satisfy the electrode design considerations (e.g., BAT volume to be stimulated, intensity of electrical stimulation signal, etc.). For instance, the object body piercing may be a straight bar/rod with enlarged ends to secure it in place as well as provide a connection means for attachment of the electrical leads.

In any of the embodiments described herein, a preliminary acquired image such as a Computed Tomography (CT), Positron Emission Tomography (PET), CT-PET, tomography, thermography, Ultrasound, Magnetic Resonance Imaging (MRI) or any other imaging technique may be a useful tool to precisely locate as a target area the subdermal BAT deposit located within the supraclavicular fossa region or BAT depot in other areas of the body. Once the precise target area has been identified using the acquired image it may be easily identified using a marker, dye or body piercing. The precise target area ascertained via the acquired image may also be instrumental as a reference tool to adjust or customize a separate mechanical locating device and thereby insure its proper placement of the stimulation patch to stimulate the BAT within the targeted BAT depot (e.g., supraclavicular fossa region BAT depot).

One application of the transdermal electrical patch for stimulation of the BAT in the supraclavicular fossa in accordance with the present invention is as an aid in inducing weight loss. Three predominate bariatric surgical procedures available today include: Gastric Bypass (RYG); Sleeve Gastrectomy (VSG) and Gastric Band (LAGB). All of these surgical procedures have failure rates typically defined as either the inability to achieve approximately 50% Excess Weight Loss (EWL) or technical failure (e.g., surgical complication). Clinical literature assesses the failure rates for these surgical procedures in the range of approximately 10% to approximately 25%. Corrective action for EWL failure rates often entails re-operation (i.e., correcting or modifying original surgical intervention) or revision surgery (i.e., converting the original procedure to an alternative surgical procedure). Any surgical course of action subjects the patient to additional risk through surgical intervention, anesthesia, etc. The present inventive external BAT transdermal electrical stimulation patch is an alternative non-surgical revisional therapeutic procedure for EWL failure.

After performing a bariatric surgical procedure (e.g., Gastric Bypass; Sleeve Gastrectomy or Gastric Band) the patient's weight loss is monitored post-surgically over a first predetermined period of time. If the monitored weight loss over this first predetermined period of time is insufficient, a complimentary neurostimulation device for activating BAT in accordance with the present invention may be utilized while monitoring the patient's weight loss over a second predetermined period of time to improve the EWL rate.

Comorbidities typically associated with obesity may also be improved by electrical stimulation of sympathetic nerves within the supraclavicular fossa region of the human body to activate BAT deposits therein. Such comorbidities include, but are not limited to, increasing energy expenditure; reducing hyperlipidemia; controlling/treating diabetes; controlling/treating high blood pressure and increasing the speed of your metabolism (e.g., basal metabolic rate).

Thus, while there have been shown, described, and pointed out fundamental novel features of the invention as applied to a preferred embodiment thereof, it will be understood that various omissions, substitutions, and changes in the form and details of the devices illustrated, and in their operation, may be made by those skilled in the art without departing from the spirit and scope of the invention. For example, it is expressly intended that all combinations of those elements and/or steps that perform substantially the same function, in substantially the same way, to achieve the same results be within the scope of the invention. Substitutions of elements from one described embodiment to another are also fully intended and contemplated. It is also to be understood that the drawings are not necessarily drawn to scale, but that they are merely conceptual in nature. It is the intention, therefore, to be limited only as indicated by the scope of the claims appended hereto.

Every issued patent, pending patent application, publication, journal article, book or any other reference cited herein is each incorporated by reference in their entirety.

What is claimed is:

1. A method for properly self-positioning a transdermal electrical stimulation patch to activate brown adipose tissue depot in a supraclavicular fossa region of a human body, comprising the steps of:

self-positioning on the body at least a portion of the transdermal electrical stimulation patch within the supraclavicular fossa region of the body wherein the self-positioning step further comprises using a separate mechanical locating tool that references at least one of the clavicle, chin, neck, sternum, or some combination thereof to properly position the electrical stimulation patch to activate the BAT depot in the supraclavicular fossa region; and generating an electric field using the electrical stimulation patch to activate the brown adipose tissue within the supraclavicular fossa region of the body.

2. The method in accordance with claim 1, wherein the mechanical locating tool references some combination of the clavicle, chin, sternum, trapezius and bones.

3. The method in accordance with claim 1, wherein the self-positioning step comprises substantially aligning at least one window or opening defined in the patch with the one or more anatomical points on the body or a corresponding marking on the body.

4. The method in accordance with claim 1, wherein the patch has a plurality of discrete adhesive pads; and, the method further comprising the step of rotating the patch to reorient the adhesive pads while the position of the patch on the body remains unchanged.

5. The method in accordance with claim 1, wherein the patch includes more than one electrode; and when properly positioned on the body, all of the electrodes lay within the supraclavicular fossa region.

6. The method in accordance with claim 1, wherein the patch includes more than one electrode; and when properly positioned on the body all of the electrodes, electronics and power source lay within the supraclavicular fossa region.

7. The method in accordance with claim 1, wherein the patch includes more than one electrode; and when properly positioned on the body at least one electrode lay within the supraclavicular fossa region, while some combination of one or more electrodes, electronics and a power source lay outside the supraclavicular fossa region.

8. The method in accordance with claim 1, wherein the patch includes more than one electrode; and when properly positioned on the body all of the electrodes, electronics and a power source lay outside the supraclavicular fossa region.

9. The method in accordance with claim 1, wherein the patch is configured so that when properly positioned on the body it straddles the clavicle or extends front-to-back over the shoulder.

10. The method in accordance with claim 1, wherein the patch includes more than one electrode; and when the patch is properly positioned on the body the electrodes are disposed in more than one plane.

* * * * *